(12) United States Patent
Bhattacharya et al.

(10) Patent No.: US 10,774,043 B2
(45) Date of Patent: Sep. 15, 2020

(54) GLYCOLACTAM COMPOUNDS, PROCESS FOR PREPARATION AND USES THEREOF

(71) Applicant: COUNCIL OF SCIENTIFIC & INDUSTRIAL RESEARCH, New Delhi (IN)

(72) Inventors: Asish Kumar Bhattacharya, Maharashtra (IN); Hemender Rami Chand, Maharashtra (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 46 days.

(21) Appl. No.: 16/099,038

(22) PCT Filed: May 5, 2017

(86) PCT No.: PCT/IN2017/050163
§ 371 (c)(1),
(2) Date: Nov. 5, 2018

(87) PCT Pub. No.: WO2017/191657
PCT Pub. Date: Nov. 9, 2017

(65) Prior Publication Data
US 2019/0194133 A1    Jun. 27, 2019

(30) Foreign Application Priority Data
May 6, 2016   (IN) .............................. 201611015813

(51) Int. Cl.
*C07D 211/76* (2006.01)
(52) U.S. Cl.
CPC .................................. *C07D 211/76* (2013.01)
(58) Field of Classification Search
None
See application file for complete search history.

(56) References Cited

U.S. PATENT DOCUMENTS

| | | |
|---|---|---|
| 5,326,880 A | 7/1994 | Mandella et al. |
| 5,994,562 A | 11/1999 | Ebel et al. |
| 6,559,150 B2 | 5/2003 | Carpino |
| 8,501,963 B2 | 8/2013 | Werpy et al. |

FOREIGN PATENT DOCUMENTS

WO       2015/170339 A1    11/2015

OTHER PUBLICATIONS

Hayashi et al, Chemical Abstracts 110:192608, Abstract of Journal of Fluorine Chemistry (1988), 41(2), 213-25 (Year: 1989).*

International Search Report for PCT/IN2017/050163 dated Aug. 24, 2017.
Gregory R. Cook, et al. "Construction of Hydroxylated Alkaloids (racemic)-Mannonolactam, (racemic)-Deoxymannojirimycin, and (racemic)-Prosopinine through Aza-Annulation," J. Org. Chem., vol. 59, No. 13, pp. 3575-3584 (Jan. 1, 1994).
Pierluigi Cartmella, et al., "Cycloaddition of Nitrile Oxides to Cyclic and Acyclic alpha, beta-Unsatuarated Amides, Frontier Orbital Interactions and an Unexpected Steric Drift Determine Regiochemistry," Tetrahedron, vol. 55, No. 22, pp. 7027-7044 (May 28, 1999).
Chau-der Li, et al., "Induction of Differentiation of Leukemia Cells in Vitro by N-Substituited Amides, Lactams, and 2-Pyridones," J. Med. Chem., vol. 24, No. 9, pp. 1092-1094 (Jan. 1, 1981).
Hans-Josef Altenbach, et al., "Stereocontrolled Synthesis of 1,5-Dideoxy~1,5~imino-allitol (1-Deoxy-allonojirimycin) from Serine," Tetrahedron: Asymmetry, vol. 6, No. 5, pp. 1077-1080 (May 1, 1995).
Rui Fu, et al., "Asymmetric syntheses of 6-deoxyfagomin, D-deoxyrhamnojirimycin, and D-rhamnono-1,5-lactam," Tetrahedron, vol. 65, No. 47, pp. 9765-9771 (Nov. 21, 2009).
J. Albert Diez, et al., "Stereoselective synthesis and biological evaluation of D-fagomine, D-3-epi-fagomine and D-3,4-epi-fagomine analongs from D-glyceraldehyde acetonide as a common building block," Org. Biomol. Chem., vol. 10, pp 9278-9286 (Jan. 1, 2012).
Tony K. M. Shing, et al., "Ruthenium-Catalyzed cis-Dihydroxylation of Alkenes: Scope and Limitations," Chem. Eur. J., vol. 2, No. 1, pp. 50-57 (Jan. 1, 1996).
Zhenqian Fu, et al., "Access to Oxoquinoline Heterocycles by N-Heterocyclic Carbene Catalyzed Ester Activation for Selective Reaction with an Enone," Angewandte Chem., vol. 53, pp. 6508-6510 (May 18, 2014).

* cited by examiner

*Primary Examiner* — Zinna Northington Davis
(74) *Attorney, Agent, or Firm* — Abelman, Frayne & Schwab

(57) ABSTRACT

The present invention discloses compounds of Formula I,

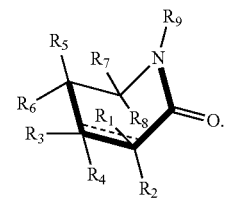

wherein each of $R_1$, $R_2$, $R_3$, $R_4$, $R_5$, $R_6$, $R_7$ and $R_8$ are independently selected from H, OBn, OH, $CH_2OBn$, $CH_2OH$, $CH_3$; $R_9$ is selected from alkyl, substituted alkyl, hydroxyl alkyl, alkenyl, benzyl; process for preparation of N-alkylated glycolactam compounds of Formula I and their use for the synthesis of piperidine alkaloids and their analogues.

9 Claims, No Drawings

GLYCOLACTAM COMPOUNDS, PROCESS FOR PREPARATION AND USES THEREOF

FIELD OF THE INVENTION

The present invention relates to glycolactam compounds. More particularly, the present invention relates to N-alkylated glycolactam compounds and process for preparation thereof. The present invention further relates to a process for the preparation of bioactive piperidine alkaloids and their analogues from glycolactam compounds.

BACKGROUND AND PRIOR ART OF THE INVENTION

Azasugar inhibitors of glycosidases and related enzymes are the subject of intense current interest. Polyhydroxylated piperidines and their synthetic analogues have attracted a great deal of attention in recent years due to their ability to mimic sugars, and competitively and selectively inhibit glycosidases and glycosyltransferases, the carbohydrate processing enzymes. These attributes make hydroxylated piperidines (azasugars) likely therapeutic agents for the treatment of diseases related to metabolic disorders involving carbohydrates such as diabetes, cancer, AIDS, and viral infections, where glycoprotein processing is crucial.

Delta-substituted α,β-unsaturated gamma-lactams are found among natural products, and they are useful as building blocks for the synthesis of a variety of biologically active compounds. Due to their conformational rigidity, reactions at the double bond, notably cycloadditions and conjugate additions, proceed with a high degree of stereocontrol.

US 2011/0263874 A1 discloses method of processing an initial compound having a formula (A)

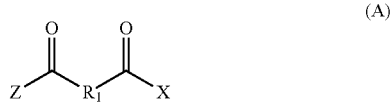

(A)

Wherein R1 comprises a saturated or unsaturated, branched or un-branched group containing from 1 to 10 carbon atoms, and Wherein Z and X independently comprise one or more of C, H, O, N, S, a halide, and a counter-ion, the method comprising: converting the initial compound to a cyclic compound having a formula (B)

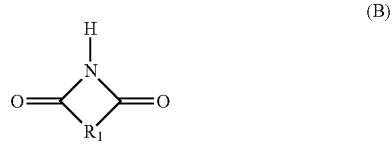

(B)

the converting comprising one or both of thermal and catalytic processing, the cyclic compound being present in a mixture comprising one or more additional components; and performing a purification to remove at least some of the one or more additional components.

U.S. Pat. No. 5,326,880 discloses asymmetrical polyvinyl pyrrolidonyl compounds and their uses as complexing and dispersing agents. Included two asymmetrical molecules, 1-methyl-3,6-dioxa-1,8-dipyrrolidonyl octane, which has two ether linkages, and N-ethylpyrrolidonyl-pyrrolidonyl-polyoxypropylene, which has two or three ether linkages.

U.S. Pat. No. 6,559,150 B2 discloses that amide can be alkylated by deprotonation with a strong base such as sodium hydride, LHMDS, or KHMDS in a suitable solvent such as DMF or THF followed by treatment with an alkylating agent such as an alkyl halide, mesylate or tosylate.

U.S. Pat. No. 5,994,562 discloses a process for preparing N-alkenylcarbox amides by dehydration of N-(2-hydroxyalkyl)carboxamides and/or diethers. Dehydration of HEP with undoped catalysts yielded bis-N-etylpyrrolidone ether as an unwanted side product at concentrations up to 71%. WO 2015170339 A1 discloses a method of synthesis of piperidine alkaloids selected from fagomine, 4-epi-fagomine and nojirimycin from tri-O-benzyl-D-glucal or tri-O-benzyl-D-galactal.

US 2011/0263874 A11/U.S. Pat. No. 8,501,963 B2 disclose the compound of formula as mentioned in the claim having no substitution in the piperidine rings at other positions. It basically involves cyclization of succinic acid derivatives to succinamide derivatives and further N alkylated pyrrolidinone derivatives using ammonia and then alkylating agent.

But, the present invention does not use ammonia and the starting material is cyclic compound (derived from carbohydrate) and by varying the conditions it gives different products as evident from scheme 1.

U.S. Pat. No. 5,326,880 disclose the compound of formula as mentioned in the claim which has no substitution on the pyrrolidone/piperidone rings at other positions, only polypyrrolidonyl compounds are synthesized from butyrolactone and substituted amine derivatives.

But, the present invention does not use butyrolactone and by varying the conditions it gives different product as shown in scheme 1. Instead the starting material is from carbohydrate.

U.S. Pat. No. 6,559,150 B2 discloses that amide can be alkylated by deprotonation with a strong base such as sodium hydride, LHMDS, or KHMDS in a suitable solvent such as DMF or THF followed by treatment with an alkylating agent such as an alkyl halide, mesylate or tosylate.

But, the present invention provides process in which varying the concentration of base not only gives the alkylated product but also an elimination product viz. α,β-unsaturated amides are formed, as shown in scheme 1.

U.S. Pat. No. 5,994,562 discloses a process for preparing N-alkenylcarbox amides by dehydration of N-(2-hydroxyalkyl)carboxamides and/or diethers. Dehydration of HEP with undoped catalysts yielded bis-N-etylpyrrolidone ether as an unwanted side product at concentrations up to 71%.

This has no correlation with the present invention wherein our process is non-catalytic for the synthesis of N-alkylpiperidine alkaloids.

There exists a commercial and industrial need for materials that exhibit excellent solvency and solvent compatibility/miscibility that also provide an improved safety profile. These are the objectives of the present invention, and to describe these lactam compounds, their compositions and uses thereof.

OBJECTS OF THE INVENTION

The main objective of the present invention is to provide N-alkylated glycolactam compounds.

Another objective of the present invention is to provide a process for the preparation of N-alkylated glycolactam compounds.

Still another objective of the present invention is to provide a process for the synthesis of bioactive piperidine alkaloids and their analogues from glycolactam compounds.

SUMMARY OF THE INVENTION

Accordingly, the present invention provides N-alkylated glycolactam compounds and process for the preparation of N-alkylated glycolactam compounds. Further, the present invention provides a process for the synthesis of bioactive piperidine alkaloids and their analogues from glycolactam compounds.

In an embodiment, the present invention provides N-alkylated glycolactam compounds of Formula (I),

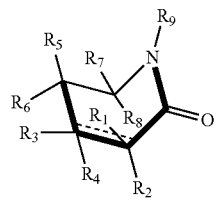

wherein each of $R_1$, $R_2$, $R_3$, $R_4$, $R_5$, $R_6$, $R_7$ and $R_8$ are independently selected from H, OBn, OH, $CH_2OBn$, $CH_2OH$, $CH_3$;
$R_9$ is selected from alkyl, substituted alkyl, alkenyl, hydroxyl alkyl, benzyl.

In an embodiment, the present invention provides N-alkylated glycolactam compounds of Formula (I) is,

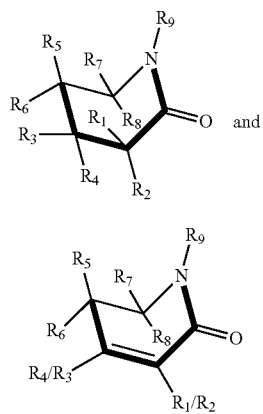

wherein each of $R_1$, $R_2$, $R_3$, $R_4$, $R_5$, $R_6$, $R_7$ and $R_8$ are independently selected from H, OBn, OH, $CH_2OBn$, $CH_2OH$, $CH_3$;
$R_9$ is selected from alkyl, substituted alkyl, alkenyl, hydroxyl alkyl, benzyl.

In an embodiment, the present invention provides a process for preparation of N-alkylated glycolactam compounds of Formula (I) comprising the steps of:
a) adding metal hydride to a solution of glycolactamin suitable solvent at temperature ranging from 0° C. to 5° C. followed by stirring reaction mixture at temperature ranging from 0° C. to 5° C. for a time period ranging from 10 to 15 mins;
b) adding alkyl halide to a reaction mixture of step (a) at temperature ranging from 0° C. to 5° C. followed by stirring reaction mixture at temperature ranging from 0° C. to 5° C. for a time period ranging from 2-48 h to afford glycolactam compounds of Formula (I).

In a preferred embodiment, said metal hydride is selected from sodium hydride, potassium hydride or calcium hydride.

In another preferred embodiment, said solvent of step (a) is selected from dimethyl formamide, dimethyl sulfoxide or tetrahydrofuran.

In yet another preferred embodiment, said alkyl halide is selected from methyl iodide, ethyl bromide, allyl bromide, n-butyl iodide, benzyl bromide, n-propyl bromide or benzyloxy 2-ethyliodide.

In yet another embodiment, the present invention provides a process for the synthesis of bioactive piperidine alkaloids and their analogues from glycolactam compounds of Formula (I).

DETAILED DESCRIPTION OF THE INVENTION

The invention will now be described in detail in connection with certain preferred and optional embodiments, so that various aspects thereof may be more fully understood and appreciated.

In view of above, the present invention provides N-alkylated glycolactam compounds and process for the preparation of N-alkylated glycolactam compounds.

In view of above, the present invention further provides a process for the synthesis of bioactive piperidine alkaloids and their analogues from glycolactam compounds.

In an embodiment, the present invention provides N-alkylated glycolactam compounds of Formula (I),

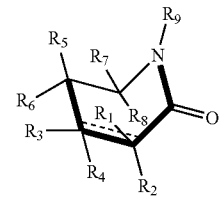

wherein each of $R_1$, $R_2$, $R_3$, $R_4$, $R_5$, $R_6$, $R_7$ and $R_8$ are independently selected from H, OBn, OH, $CH_2OBn$, $CH_2OH$, $CH_3$;
$R_9$ is selected from alkyl, substituted alkyl, alkenyl, hydroxyl alkyl, benzyl.
Wherein formula I is

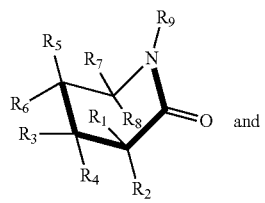

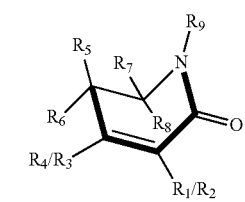

wherein each of $R_1$, $R_2$, $R_3$, $R_4$, $R_5$, $R_6$, $R_7$ and $R_8$ are independently selected from H, OBn, OH, CH$_2$OBn, CH$_2$OH, CH$_3$;

$R_9$ is selected from alkyl, substituted alkyl, alkenyl, hydroxyl alkyl, benzyl.

In another embodiment, the present invention provides to regioselective process for preparation of N-alkylated glycolactam compounds of Formula (I) comprising the steps of:
a) adding metal hydride to a solution of glycolactam compounds in suitable solvent at temperature ranging from 0° C. to 5° C. followed by stirring reaction mixture at 0° C. to 5° C. for a time period ranging from 10 to 15 mins;
b) adding alkyl halide to a reaction mixture of step (a) at temperature ranging from 0° C. to 5° C. followed by stirring reaction mixture at 0° C. to 5° C. for a time period ranging from 2 to 48 h to afford glycolactam compounds of Formula (I).

In a preferred embodiment, said metal hydride is selected from sodium hydride, potassium hydride or calcium hydride.

In another preferred embodiment, solvent of step (a) is selected from dimethyl formamide, dimethyl sulfoxide, and tetrahydrofuran.

In still another preferred embodiment, alkyl halide is selected from methyl iodide, ethyl bromide, allyl bromide, n-butyl iodide, benzyl bromide, n-propyl bromide or benzyloxy 2-ethyliodide.

The process for the preparation of N-alkylated glycolactam compounds of Formula (I) is as depicted below in scheme 1:

Scheme-1

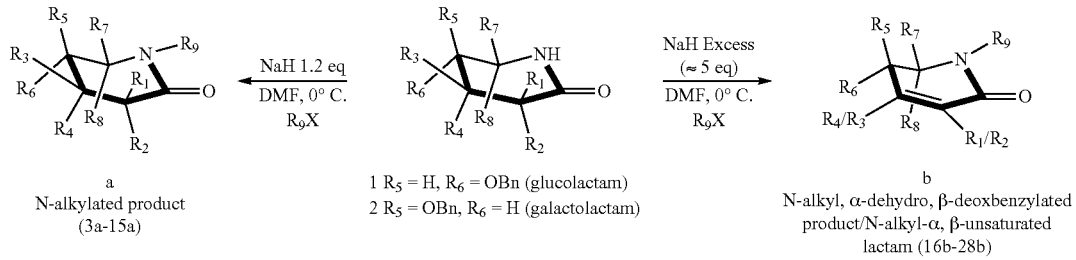

a
N-alkylated product
(3a-15a)

1 $R_5$ = H, $R_6$ = OBn (glucolactam)
2 $R_5$ = OBn, $R_6$ = H (galactolactam)

b
N-alkyl, α-dehydro, β-deoxbenzylated product/N-alkyl-α, β-unsaturated lactam (16b-28b)

3a $R_1$, $R_2$, $R_4$, $R_8$ = H, $R_3$ = OBn, $R_7$ = CH$_2$OBn, $R_5$ = H, $R_6$ = OBn, $R_9$ = CH$_3$
4a $R_1$, $R_2$, $R_4$, $R_8$ = H, $R_3$ = OBn, $R_7$ = CH$_2$OBn, $R_5$ = OBn, $R_6$ = H, $R_9$ = CH$_3$
5a $R_1$, $R_2$, $R_4$, $R_8$ = H, $R_3$ = OBn, $R_7$ = CH$_2$OBn, $R_5$ = H, $R_6$ = OBn, $R_9$ = CH$_2$CH$_3$
6a $R_1$, $R_2$, $R_4$, $R_8$ = H, $R_3$ = OBn, $R_7$ = CH$_2$OBn, $R_5$ = OBn, $R_6$ = H, $R_9$ = CH$_2$CH$_3$
7a $R_1$, $R_2$, $R_4$, $R_8$ = H, $R_3$ = OBn, $R_7$ = CH$_2$OBn, $R_5$ = H, $R_6$ = OBn, $R_9$ = CH$_2$CH$_2$CH$_3$
8a $R_1$, $R_2$, $R_4$, $R_8$ = H, $R_3$ = OBn, $R_7$ = CH$_2$OBn, $R_5$ = OBn, $R_6$ = H, $R_9$ = CH$_2$CH$_2$CH$_3$
9a $R_1$, $R_2$, $R_4$, $R_8$ = H, $R_3$ = OBn, $R_7$ = CH$_2$OBn, $R_5$ = H, $R_6$ = OBn, $R_9$ = CH$_2$CH$_2$CH$_2$CH$_3$
10a $R_1$, $R_2$, $R_4$, $R_8$ = H, $R_3$ = OBn, $R_7$ = CH$_2$OBn, $R_5$ = OBn, $R_6$ = H, $R_9$ = CH$_2$CH$_2$CH$_2$CH$_3$
11a $R_1$, $R_2$, $R_4$, $R_8$ = H, $R_3$ = OBn, $R_7$ = CH$_2$OBn, $R_5$ = H, $R_6$ = OBn, $R_9$ = CH$_2$Ph
12a $R_1$, $R_2$, $R_4$, $R_8$ = H, $R_3$ = OBn, $R_7$ = CH$_2$OBn, $R_5$ = H, $R_6$ = OBn, $R_9$ = Allyl
13a $R_1$, $R_2$, $R_4$, $R_8$ = H, $R_3$ = OBn, $R_7$ = CH$_2$OBn, $R_5$ = OBn, $R_6$ = H, $R_9$ = Allyl
14a $R_1$, $R_2$, $R_4$, $R_8$ = H, $R_3$ = OBn, $R_7$ = CH$_2$OBn, $R_5$ = H, $R_6$ = OBn, $R_9$ = CH$_2$CH$_2$OBn
15a $R_1$, $R_2$, $R_4$, $R_8$ = H, $R_3$ = OBn, $R_7$ = CH$_2$OBn, $R_5$ = OBn, $R_6$ = H, $R_9$ = CH$_2$CH$_2$OBn
16b $R_1$, $R_2$, $R_3$, $R_4$, $R_8$ = H, $R_7$ = CH$_2$OBn, $R_5$ = H, $R_6$ = OBn, $R_9$ = CH$_3$
17b $R_1$, $R_2$, $R_3$, $R_4$, $R_8$ = H, $R_7$ = CH$_2$OBn, $R_5$ = OBn, $R_6$ = H, $R_9$ = CH$_3$
18b $R_1$, $R_2$, $R_3$, $R_4$, $R_8$ = H, $R_7$ = CH$_2$OBn, $R_5$ = H, $R_6$ = OBn, $R_9$ = CH$_2$CH$_3$
19b $R_1$, $R_2$, $R_3$, $R_4$, $R_8$ = H, $R_7$ = CH$_2$OBn, $R_5$ = OBn, $R_6$ = H, $R_9$ = CH$_2$CH$_3$
20b $R_1$, $R_2$, $R_3$, $R_4$, $R_8$ = H, $R_7$ = CH$_2$OBn, $R_5$ = H, $R_6$ = OBn, $R_9$ = CH$_2$CH$_2$CH$_3$
21b $R_1$, $R_2$, $R_3$, $R_4$, $R_8$ = H, $R_7$ = CH$_2$OBn, $R_5$ = OBn, $R_6$ = H, $R_9$ = CH$_2$CH$_2$CH$_3$
22b $R_1$, $R_2$, $R_3$, $R_4$, $R_8$ = H, $R_7$ = CH$_2$OBn, $R_5$ = H, $R_6$ = OBn, $R_9$ = CH$_2$CH$_2$CH$_2$CH$_3$
23b $R_1$, $R_2$, $R_3$, $R_4$, $R_8$ = H, $R_7$ = CH$_2$OBn, $R_5$ = OBn, $R_6$ = H, $R_9$ = CH$_2$CH$_2$CH$_2$CH$_3$
24b $R_1$, $R_2$, $R_3$, $R_4$, $R_8$ = H, $R_7$ = CH$_2$OBn, $R_5$ = H, $R_6$ = OBn, $R_9$ = CH$_2$Ph
25b $R_1$, $R_2$, $R_3$, $R_4$, $R_8$ = H, $R_7$ = CH$_2$OBn, $R_5$ = H, $R_6$ = OBn, $R_9$ = Allyl
26b $R_1$, $R_2$, $R_3$, $R_4$, $R_8$ = H, $R_7$ = CH$_2$OBn, $R_5$ = OBn, $R_6$ = H, $R_9$ = Allyl
27b $R_1$, $R_2$, $R_3$, $R_4$, $R_8$ = H, $R_7$ = CH$_2$OBn, $R_1$, $R_2$, $R_3$, $R_4$, $R_8$ = H, $R_7$ = CH$_2$OBn, $R_5$ = H, $R_6$ = OBn, $R_9$ = CH$_2$CH$_2$OBn
28b $R_1$, $R_2$, $R_3$, $R_4$, $R_8$ = H, $R_7$ = CH$_2$OBn, $R_5$ = OBn, $R_6$ = H, $R_9$ = CH$_2$CH$_2$OBn

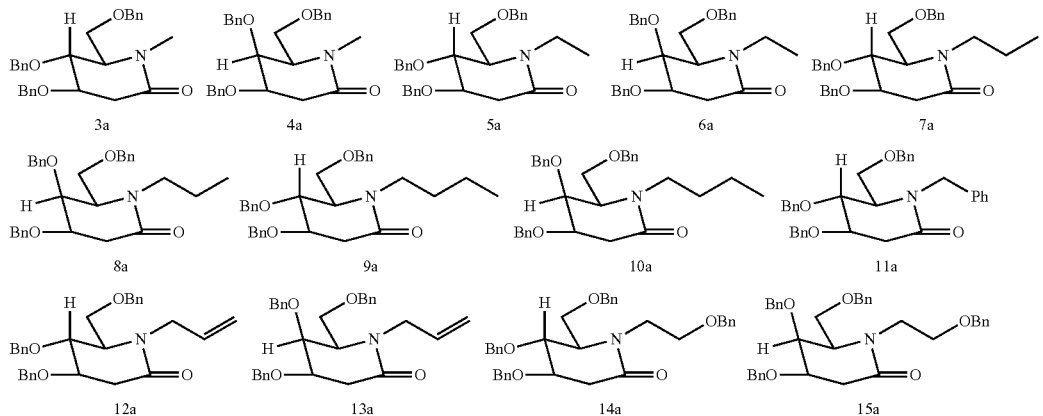

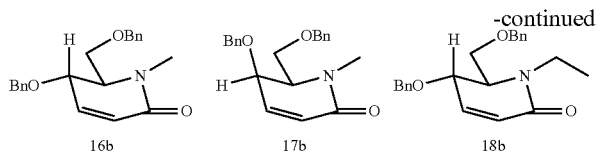
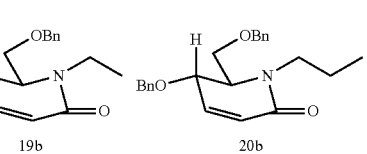
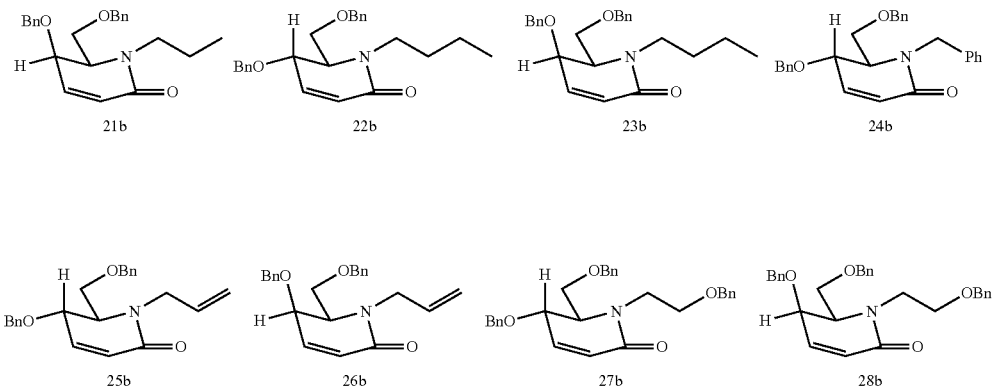

In another embodiment, the present invention provides a process for the synthesis of bioactive piperidine alkaloids and their analogues from glycolactam compounds of Formula (I).

In a preferred embodiment, said bioactive piperidine alkaloids and their analogues are selected from Mannolactam, Deoxymannojirimycin, N-butyl deoxymannojirimycinMiglustat, N-(2-hydroxyethyl)deoxymannojirimycin-Miglitol, (+)-Prosophylline, (+)-Prosopinine, 3-epi-N-butyl deoxymannojirimycin, 3-epi-N-(2-hydroxyethyl)deoxymannojirimycin.

In another preferred embodiment, the present invention relates to a dihydroxylation of glycolactam compounds of Formula (I) comprising the steps of:
a) adding a solution of Ruthenium (III) chloride hydrate (RuCl$_3$.3H$_2$O) and Sodium periodate (NaIO$_4$) in distilled water to a solution of glycolactam compounds of Formula (IB) in acetonitrile at the temperature ranging of 0° C. to 5° C.;
b) stirring the reaction mixture of step (a) for a time period ranging from 30 to 40 minutes at the temperature ranging from 0° C. to 5° C. to afford dihydroxylated compound of glycolactam compounds of Formula (IB).

In yet another preferred embodiment, the present invention relates to process for the preparation of Mannolactam comprising the steps of:
a) adding a solution of Ruthenium (III) chloride hydrate (RuCl$_3$.3H$_2$O) and Sodium periodate (NaIO$_4$) in distilled water to a solution of glycolactam compounds of Formula (IB) in acetonitrile at the temperature ranging of 0° C. to 5° C.;
b) stirring the reaction mixture of step (a) for a time period ranging from 30 to 40 minutes at the temperature ranging from 0° C. to 5° C. to afford dihydroxylated compound of glycolactam compounds of Formula (IB).
c) adding Pd/C to a solution of said dihydroxylated glycolactam compounds of Formula (I) in methanol/ethanol/ethyl acetate followed by stirring for the time period ranging from 14-16 h at the temperature ranging from 30-35° C. under hydrogen atmosphere to afford Mannolactam.

In still another preferred embodiment, the present invention relates to process for the preparation of Deoxymannojirimycin comprising the steps of:
a) adding borane dimethyl sulphide (BH$_3$.DMS) to a solution of dihydroxylated compound of a glycolactam compounds of Formula (IB) in suitable solvent at the temperature ranging from 0° C. to 5° C. for 1-2 h followed by stirring at room temperature ranging from 30-35° C. for 4-6 h followed further by stirring at refluxing the reaction mixture at temperature ranging from 80° C. to 85° C. for a time period ranging from 2 to 4 hours to obtain a dihyroxylated piperidine derivatives of formula IB;
b) adding Pd/C to a solution of said dihyroxylated piperidine derivatives of formula IB in methanol/ethanol/ethyl acetate followed by stirring for the time period ranging from 14-16 h at the temperature ranging from 30-35° C. under hydrogen atmosphere to afford Deoxymannojirimycin.

In a more preferred embodiment, said solvent of step (a) is selected from tetrahydrofuran or dioxane.

The processes for the preparation of Mannolactam and Deoxymannojirimycinare as depicted in scheme 2 below:

Scheme 2.

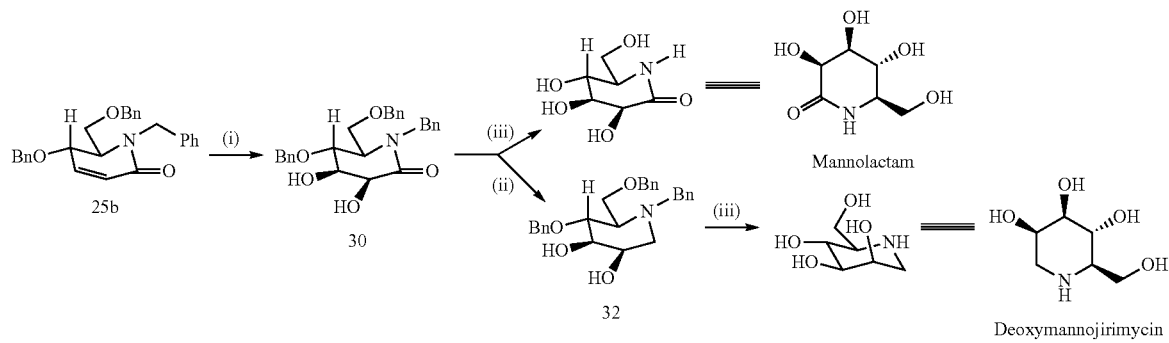

Reagents and conditions: (i) RuCl₃, NaIO₄, CH₃CN:H₂O (6:1), 0-5° C., 35 min (ii) BH₃·DMS THF, 0° C., rt, reflux (iii) H₂, Pd/C, MeOH, 30-35° C., 14-16 h.

In still yet another preferred embodiment, the present invention provides a process for preparation of N-butyl deoxynojirimycin and N-(2-hydroethyl deoxynojirimycin via the hydrolysis of protected glycolactam compounds of Formula (I) comprising the steps of:

a) adding a solution of Ruthenium (III) chloride hydrate (RuCl₃.3H₂O) and NaIO₄ in distilled water to a solution of glycolactam compounds of Formula (IB) in acetonitrile at the temperature ranging of 0° C. to 5° C.;
b) stirring the reaction mixture of step (a) for the time ranging from 30 to 40 minutes at the temperature ranging from 0 to 5° C. to afford dihydroxylated compound of a glycolactam compounds of Formula (IB);
c) adding borane dimethyl sulphide (BH₃.DMS) to a solution of dihydroxylated compound of a glycolactam compounds of Formula (IB) in suitable solvent at the temperature ranging from 0° C. to 5° C. for 1-2 h followed by stirring at room temperature ranging from 30-35° C. for 4-6 h followed further by stirring at refluxing the reaction mixture at temperature ranging from 80° C. to 85° C. for a time period ranging from 2 to 4 hours to obtain dihyroxylated piperidine derivatives of formula IB;
d) hydrogenating of product of step c by hydrogenating agent in suitable solvent to afford desired product.

In a more preferred embodiment, said solvent of step (c) is selected from tetrahydrofuran, dioxane.

In another more preferred embodiment, said hydrogenating agent of step (d) is hydrogen and palladium on carbon (H₂, Pd/C).

In yet another more preferred embodiment, said solvent of step (d) is selected from alcohol, esters preferably methanol, ethanol or ethyl acetate.

The processes for the preparation of N-butyl deoxynojirimycin and N-(2-hydroethyl deoxynojirimycin are as depicted in Scheme 3 below:

Scheme 3.

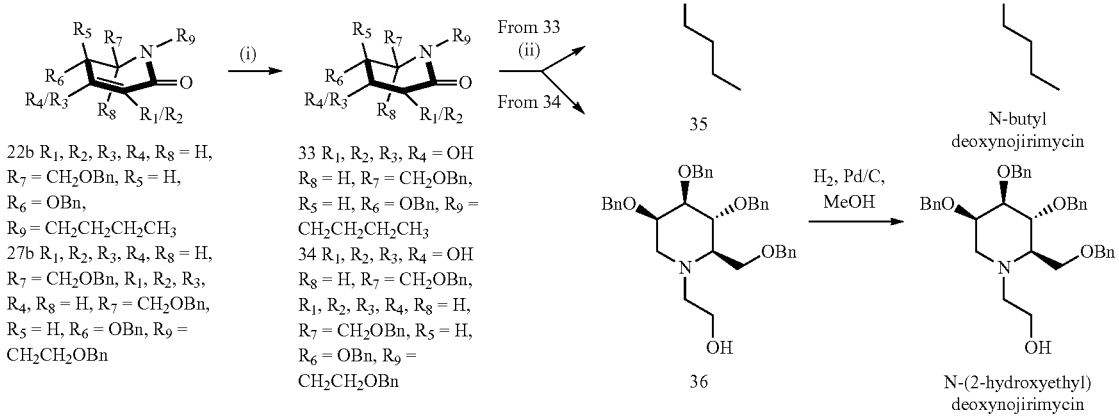

22b R₁, R₂, R₃, R₄, R₈ = H,
R₇ = CH₂OBn, R₅ = H,
R₆ = OBn,
R₉ = CH₂CH₂CH₂CH₃
27b R₁, R₂, R₃, R₄, R₈ = H,
R₇ = CH₂OBn, R₁, R₂, R₃,
R₄, R₈ = H, R₇ = CH₂OBn,
R₅ = H, R₆ = OBn, R₉ =
CH₂CH₂OBn

33 R₁, R₂, R₃, R₄ = OH
R₈ = H, R₇ = CH₂OBn,
R₅ = H, R₆ = OBn, R₉ =
CH₂CH₂CH₂CH₃
34 R₁, R₂, R₃, R₄ = OH
R₈ = H, R₇ = CH₂OBn,
R₁, R₂, R₃, R₄, R₈ = H,
R₇ = CH₂OBn, R₅ = H,
R₆ = OBn, R₉ =
CH₂CH₂OBn

Reagents and conditions: (i) RuCl₃, NaIO₄, CH₃CN:H₂O (6:1), 0-5° C., 35 min (ii) BH₃·DMS THF, 0° C., rt, reflux.

In still another preferred embodiment, the present invention relates to preparation of (+)-Prosopinine comprising the steps of:

a) adding Nickel(II) Chloride Hexahydrate (NiCl$_2$.6H$_2$O) to a cooled solution of a glycolactam compounds of Formula (IB) in alcohol followed by stirring for 10 to 15 mins at the temperature ranging from 0° C. to 5° C.;
b) adding sodium borohydride (NaBH$_4$) to a solution of step (a) at the temperature ranging from 0° C. to 5° C. for a time period ranging from 10 to 15 mins; followed by stirring for 2 to 2.5 h at the room temperature ranging from 25 to 30° C. to afford saturated glycolatum of compound of formula IB;
c) adding Lawesson's reagent to a solution of product of step (b) in THF or dioxane followed by stirring the mixture for the time period ranging from 4-12 h to afford saturated thiolactum of compound of formula IB;
d) stirring the solution of said thiolactam of step (c) and 1-Bromoethyl acetate in diethylether or dichloromethane for the time period ranging from 24-36 h, removing the solvent to afford the thionium salt, adding triphenylphosphine (PPh$_3$) to a solution of said thionium salt in acetonitrile followed by stirring for the time period ranging from 10 to 15 mins. further adding triethyl amine to the reaction mixture followed by heating at the temperature ranging from 70-75° C. for the time period ranging from 26 to 27 h, filtering the product enamide;
e) adding sodium cyanoborohydride to a solution of the enaminoester and bromocresol green (trace amounts as an indicator) in methanol, adding 5% methanolic HCl solution dropwise until a yellow color persisted in solution, stirring the reaction mixture for the time ranging from 2 to 3 h, periodic adding HCl to maintain a yellow color, diluting the mixture with CH$_2$Cl$_2$, washing with 10% aqueous NaHCO$_3$ to afford piperidines;
f) adding Lithium aluminum hydride (LiAlH$_4$) to a solution of said ester of step (e) in diethylether (Et$_2$O) or tetrahydrofuran (THF) followed by stirring for the time period ranging from 2-4 h; quenching by addition of water, 15% aqueous sodium hydroxide (NaOH) followed by stirring for 1 h filtering the solution to afford the alcohol;
g) adding a solution of dimethyl sulfoxide (DMSO) in dicholoromethane (CH$_2$Cl$_2$) a solution of oxalyl chloride in dicholoromethane at the temperature ranging from −70° C. to −80° C. for time period ranging from 10 to 11 h, adding a solution of alcohol (substrate to be reduced) in dichoromethane (CH$_2$Cl$_2$) to reaction mixture followed by stirring for 45 to 50 mins at the temperature ranging from −65° C. to −70° C., adding trimethylamine to above solution followed by stirring for the time period ranging from 20 to 30 mins at the temperature ranging from −65° C. to −70° C. and then warming to room temperature for the time period ranging from 1 to 2 hours to afford aldehyde;
h) refluxing a mixture of 2-(7-bromoheptyl)-2-ethyl-1,3-dioxolane and PPh$_3$ in toluene for the time period ranging from 40-50 h, cooling the solution to room temperature, removing the solvent and adding the tetrahydrofuran to above mixture, adding a solution of Butyl lithium (BuLi) (2.5 M in hexane) to the phoshonium salt at the temperature ranging from −78° C. to −80° C. followed by stirring for 10-20 min at −78° C. and then continuing the stirring for the time period ranging from 1-3 h at the temperature ranging from 25° C. to 30° C., cooling the resulting ylide solution to −78° C. and adding the aldehyde of step f in tetrahydrofuran (THF) followed by warming the mixture −45° C. over 2-4 h, continuing the stirring for an additional 1-2 hrs at −45° C., warming to 0° C. for 3-5 h, and stirring an additional 2-4 h at the temperature ranging from 25° C. to 30° C. to afford product of this step;
i) adding hydrochloric acid (10% aqueous HCl) to a solution of the above condensed product of step h in tetrahydrofuran(THF), followed by stirring for 2-4 h, adding saturated aqueous sodium bicarbonate (NaHCO$_3$) (10 mL) and extracting the mixture dichloromethane, drying and concentrating the organic layers to afford residue, dissolving the residue in ethanol (EtOH) or methanol (MeOH) and adding conc HCl, adding 10% Pd on carbon followed by stirring under H$_2$ (3 atm) for 20-30 h to afford (+)-Prosopinine.

In still yet another preferred embodiment, the present invention relates to preparation of (+)-Prosophylline comprising the steps of:
a) adding Nickel(II) Chloride Hexahydrate (NiCl$_2$.6H$_2$O) to a cooled solution of a glycolactam compounds of Formula (I) in alcohol followed by stirring for 10 to 15 mins at the temperature ranging from 0° C. to 5° C.;
b) adding sodium borohydride (NaBH$_4$) to a solution of step (a) at the temperature ranging from 0° C. to 5° C. for a time period ranging from 10 to 15 mins; followed by stirring for 2 to 2.5 h at the room temperature ranging from 25 to 30° C.;
c) adding Lawesson's reagent to a solution of product of step b in THF or dioxane followed by stirring the mixture for the time period ranging from 4-12 h to afford thiolactum;
d) stirring the solution of said thiolactam of step (c) and 1-Bromoethyl acetate in diethylether or dichloromethane for the time period ranging from 24-36 h, removing the solvent to afford the thionium salt, adding PPh$_3$ to a solution of said thionium salt in acetonitrile followed by stirring for the time period ranging from 10 to 15 mins. further adding triethyl amine to the reaction mixture followed by heating at the temperature ranging from 70-75° C. for the time period ranging from 26 to 27 h, filtering the product enamide;
e) stirring the mixture of enamide of step d, sodium carbonate (Na$_2$CO$_3$) and 10% Palladium on carbon (Pd/C) (0.1 g/mmol enamide) in ethanol (EtOH) or methanol (MeOH) under an atmosphere of hydrogen (H$_2$) (1-3 atm) for the time period ranging from 16-48 h to with sodium cyanoborohydride under acidic pH to afford an ester;
f) adding lithium aluminum hydride (LiAlH$_4$) to a solution of the piperidine of step e in diethylether (Et$_2$O) or tetrahydrofuran (THF), followed by stirring the time ranging from 2-4 h, quenching the reaction by addition of water, 15% aqueous NaOH, stirring the mixture for the time ranging from 1 h to 2 h to afford alcohol;
g) adding a solution of DMSO in CH$_2$Cl$_2$ to a solution of oxalyl chloride in CH$_2$Cl$_2$ at the temperature ranging from −70° C. to −80° C. for the time period ranging from 10 to 11 h, adding a solution of alcohol (substrate to be reduced) in CH$_2$Cl$_2$ to above mixture, allowing to stir for time ranging from 45 to 50 mins. at the temperature ranging from −65° C. to −70° C., adding triethyl amine followed by stirring for the time ranging from 20 to 30 mins at the temperature ranging from −65° C. to −70° C., warming to 25° C. to 30° C. for the time ranging from 1 to 2 h to afford aldehyde;
h) refluxing a mixture of 2-(7-bromoheptyl)-2-ethyl-1,3-dioxolane and PPh$_3$ in toluene for the time period ranging from 40-50 h, cooling the solution to room temperature, removing the solvent and adding the tetrahydrofuran to above mixture, adding a solution of Butyl lithium (BuLi) (2.5 M in hexane) to the phoshonium salt at the temperature ranging from −78° C. to −80° C. followed by stirring for 10-20 min at −78° C.

(EtOH) or methanol (MeOH) and adding conc HCl, adding 10% Pd on carbon followed by stirring under H$_2$ (3 atm) for 20-30 h to afford (+)-Prosophylline.

The processes for the preparation of (+)-Prosophylline and (+)-Prosopinine are as depicted in scheme 4 below:

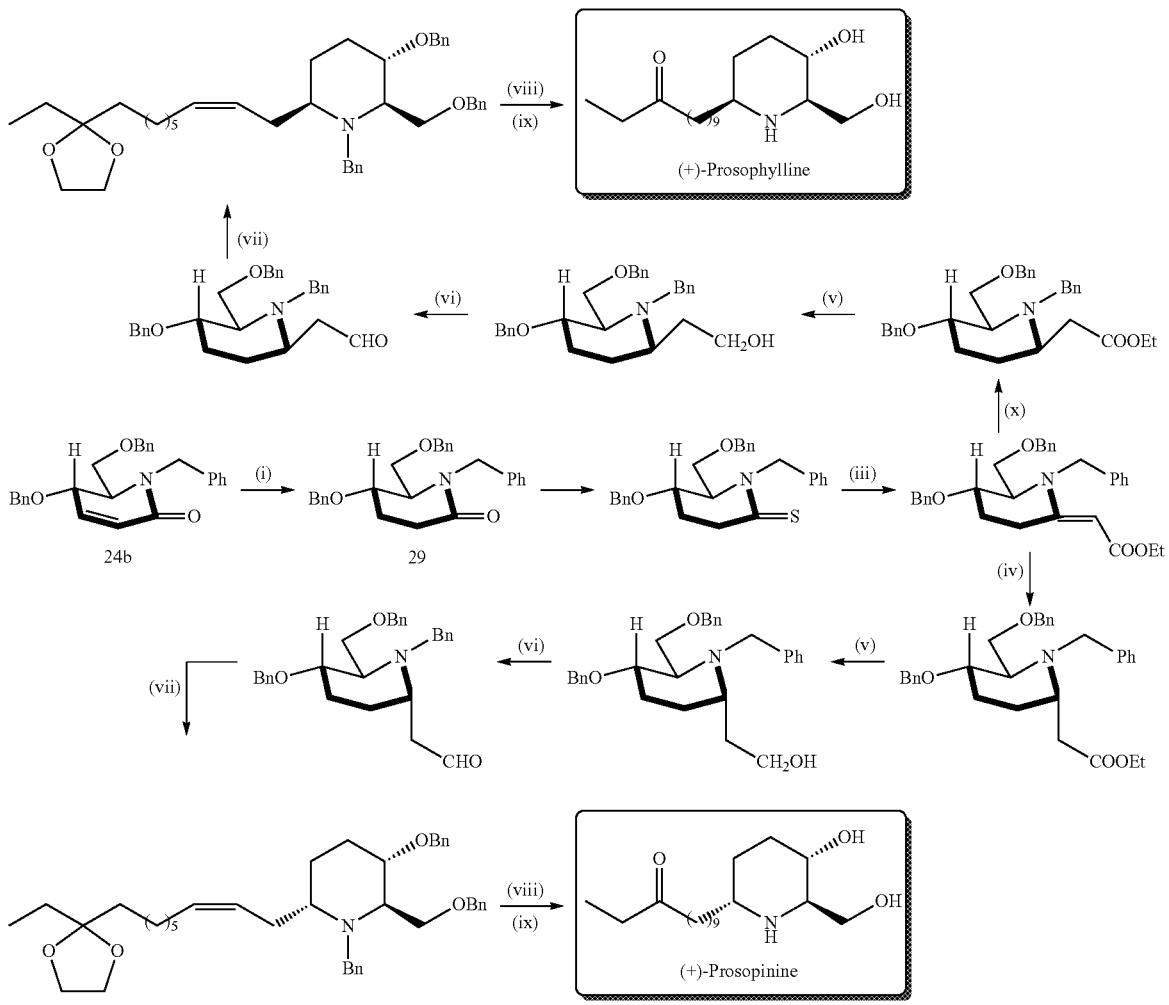

Scheme 4.

Reagents and conditions. (i) NiCl$_2$·6H$_2$O, NaBH$_4$, MeOH, 0° C. to rt, 2.5 h (ii) Lawesson's reagent, (iii) (a) Ethyl bromo acetate. (b) NEt$_3$, PPh$_3$ (iv) NaBH$_3$CN pH 4.0 (v) (a) LAH, (b) NaOH, (vi) DMSO, (COCl)$_2$, Et$_3$N. (vii) PPh$_3$, n-BuLi, 2-(7-bromoheptyl)-2-ethyl-1,3-dioxolane (viii) HCl, H$_2$O (ix) H$_2$, Pd/C, HCl. (x) H$_2$, Pd/C, Na$_2$CO$_3$, MeOH and then continuing the stirring for the time period ranging from 1-3 h at the temperature ranging from 25° C. to 30° C., cooling the the resulting ylide solution to −78° C. and adding the aldehyde of step f in tetrahydrofuran (THF) followed by warming the mixture −45° C. over 2-4 h, continuing the stirring for an additional 1-2 hrs at −45° C., warming to 0° C. for 3-5 h, and stirring an additional 2-4 h at the temperature ranging from 25° C. to 30° C. to afford product of this step;
i) adding hydrochloric acid (10% aqueous HCl) to a solution of the above condensed product of step h in tetrahydrofuran(THF), followed by stirring for 2-4 h, adding saturated aqueous sodium bicarbonate (NaHCO$_3$) (10 mL) and extracting the mixture dichloromethane, drying and concentrating the organic layers to afford residue, dissolving the residue in ethanol In an aspect, the present invention provides compound of formula I selected from:
(4R,5R,6R)-4,5-bis(benzyloxy)-6-((benzyloxy)methyl)-1-methylpiperidin-2-one (3a);
(4R,5S,6R)-4,5-bis(benzyloxy)-6-((benzyloxy)methyl)-1-methylpiperidin-2-one (4a);
(4R,5R,6R)-4,5-bis(benzyloxy)-6-((benzyloxy)methyl)-1-ethylpiperidin-2-one (5a);
(4R,5S,6R)-4,5-bis(benzyloxy)-6-((benzyloxy)methyl)-1-ethylpiperidin-2-one (6a);
(4R,5R,6R)-4,5-bis(benzyloxy)-6-((benzyloxy)methyl)-1-propyl piperidine-2-one (7a);
(4R,5S,6R)-4,5-bis(benzyloxy)-6-((benzyloxy)methyl)-1-propylpiperidin-2-one (8a);
(4R,5R,6R)-4,5-bis(benzyloxy)-6-((benzyloxy)methyl)-1-butylpiperidin-2-one (9a);

(4R,5S,6R)-4,5-bis(benzyloxy)-6-((benzyloxy)methyl)-1-butylpiperidin-2-one (10a);

(4R,5R,6R)-1-benzyl-4,5-bis(benzyloxy)-6-((benzyloxy)methyl)piperidin-2-one (11a);

(4R,5R,6R)-1-allyl-4,5-bis(benzyloxy)-6-((benzyloxy)methyl)piperidin-2-one (12a);

(4R,5S,6R)-1-allyl-4,5-bis(benzyloxy)-6-((benzyloxy)methyl)piperidin-2-one (13a);

(4R,5R,6R)-4,5-bis(benzyloxy)-1-(2-(benzyloxy)ethyl)-6-((benzyloxy)methyl)piperidin-2-one (14a);

(4R,5S,6R)-4,5-bis(benzyloxy)-1-(2-(benzyloxy)ethyl)-6-((benzyloxy)methyl)piperidin-2-one (15a);

(5S,6R)-5-(benzyloxy)-6-((benzyloxy)methyl)-1-methyl-5,6-dihydropyridin-2(1H)-one (16b);

(5R,6R)-5-(benzyloxy)-6-((benzyloxy)methyl)-1-methyl-5,6-dihydropyridin-2(1H)-one (17b);

(5S,6R)-5-(benzyloxy)-6-((benzyloxy)methyl)-1-ethyl-5,6-dihydropyridin-2(1H)-one (18b);

(5R,6R)-5-(benzyloxy)-6-((benzyloxy)methyl)-1-ethyl-5,6-dihydropyridin-2(1H)-one (19b);

(5S,6R)-5-(benzyloxy)-6-((benzyloxy)methyl)-1-propyl-5,6-dihydropyridin-2(1H)-one (20b);

(5R,6R)-5-(benzyloxy)-6-((benzyloxy)methyl)-1-propyl-5,6-dihydropyridin-2(1H)-one (21b);

(5S,6R)-5-(benzyloxy)-6-((benzyloxy)methyl)-1-butyl-5,6-dihydropyridin-2(1H)-one (22b);

(5R,6R)-5-(benzyloxy)-6-((benzyloxy)methyl)-1-butyl-5,6-dihydropyridin-2(1H)-one (23b);

(5S,6R)-1-benzyl-5-(benzyloxy)-6-((benzyloxy)methyl)-5,6-dihydropyridin-2(1H)-one (24b);

(5S,6R)-1-allyl-5-(benzyloxy)-6-((benzyloxy)methyl)-5,6-dihydropyridin-2(1H)-one (25b);

(5R,6R)-1-allyl-5-(benzyloxy)-6-((benzyloxy)methyl)-5,6-dihydropyridin-2(1H)-one (26b);

(5S,6R)-5-(benzyloxy)-1-(2-(benzyloxy)ethyl)-6-((benzyloxy)methyl)-5,6-dihydropyridin-2(1H)-one (27b);

(5R,6R)-5-(benzyloxy)-1-(2-(benzyloxy)ethyl)-6-((benzyloxy)methyl)-5,6-dihydropyridin-2(1H)-one (28b).

Examples Following examples are given by way of illustration therefore should not be construed to limit the scope of the invention.

Example 1: Synthesis of N-Alkylated Product (3a-15a)

To a solution of glycolactam (50 mg, 0.12 mmol) in 8 ml DMF at 0° C. was added NaH (60% dispersion in oil, 3.4 mg, 1.2 eq) and stirred at 0° C. for 10 min. Alkyl halide RX (2 eq) was added and stirred at 0° C. till complete consumption of starting material with periodic TLC check. Ethyl acetate (10 ml) was added followed by cold sat. NH$_4$Cl solution dropwise with vigorous stirring. The aq. layer was extracted with ethyl acetate (4×10 ml), dried, concentrated and residual nonvolatile solvent was removed by co-distillation with toluene under reduced pressure with water bath temperature not exceeding 50° C., and crude was then subjected to flash chromatography.

Example 2: (4R,5R,6R)-4,5-bis(benzyloxy)-6-((benzyloxy)methyl)-1-methylpiperidin-2-one. (3a)

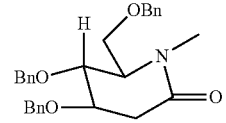

Colorless oil, C$_{28}$H$_{31}$NO$_4$, R$_f$ 0.40 (EtOAc-petroleum ether, 1:1); [α]$^{25}_D$ +10.60 (c 0.73 CHCl$_3$); IR (CHCl$_3$): ν$_{max}$ 3394, 3089, 3065, 3029, 3006, 2954, 2924, 2865, 1723, 1642, 1454, 1264, 1099, 1074, 754, 698 cm$^{-1}$; 3 d, yield 62%. Flash chromatography Elution with 20-25% EtOAc-petroleum ether; $^1$H NMR (400 MHz, CHLOROFORM-d) δ$_H$=7.35-7.24 (m, 15H), 4.73 (d, J=11.7 Hz, 1H), 4.62-4.54 (m, 2H), 4.53-4.44 (m, 1H), 4.42 (s, 2H), 3.93 (dd, J=3.8, 6.2 Hz, 1H), 3.89-3.80 (m, 1H), 3.67 (dd, J=5.5, 9.7 Hz, 1H), 3.52 (ddd, J=4.0, 9.4, 17.1 Hz, 2H), 2.92 (s, 3H), 2.79 (dd, J=4.8, 17.0 Hz, 1H), 2.50 (dd, J=7.1, 16.9 Hz, 1H); $^{13}$C NMR (100 MHz, CHLOROFORM-d) δ$_C$=168.4, 137.9, 137.8, 134.4, 128.5, 127.9, 127.9, 127.8, 127.7, 127.6, 127.6, 75.5, 75.2, 73.2, 72.9, 71.4, 68.5, 62.9, 34.8, 33.3; ESI-MS: m/z 468.14 (M+Na)$^+$; HRMS: m/z calcd for CC$_{28}$H$_{32}$NO$_4$ 446.2326, found 446.2325.

Example 3: (4R,5S,6R)-4,5-bis(benzyloxy)-6-((benzyloxy)methyl)-1-methylpiperidin-2-one. (4a)

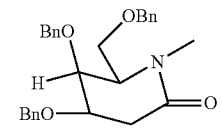

Colorless oil, C$_{28}$H$_{31}$NO$_4$, R$_f$ 0.421 (EtOAc-petroleum ether, 1:1); [α]$^{25}_D$ +12.43 (c 0.83, CHCl$_3$); IR (CHCl$_3$): ν$_{max}$ 3402, 3087, 3065, 3008, 2920, 2854, 1724, 1640, 1453, 1213, 1102, 1027, 756, 698, 667 cm$^{-1}$; 18 h, β (N—CH$_3$)+α (N—CH$_3$); yield 49% (β+α). Flash chromatography elution with 10-25% EtOAc-petroleum ether; $^1$H NMR (500 MHz, CHLOROFORM-d) δ$_H$=7.40-7.23 (m, 15H), 4.78 (d, J=11.6 Hz, 1H), 4.65-4.56 (m, 3H), 4.47 (s, 2H), 4.0-4.03 (m, 1H), 3.98 (dd, J=4.3, 9.8 Hz, 1H), 3.88 (ddd, J=1.7, 5.2, 6.9 Hz, 1H), 3.79 (dd, J=6.1, 10.1 Hz, 1H), 3.70-3.65 (m, 1H), 2.99 (s, 3H), 2.88-2.78 (m, 1H), 2.61 (dd, J=5.0, 17.2 Hz, 1H); $^{13}$C NMR (125 MHz, CHLOROFORM-d) δ$_C$=167.9, 138.0, 137.9, 128.5, 128.4, 128.4, 127.8, 127.8, 127.7, 127.6, 127.4, 74.3, 73.8, 73.4, 72.8, 71.3, 71.1, 60.8, 35.3, 33.3; ESI-MS: m/z 468.03 (M+Na)$^+$; HRMS: m/z calcd for C$_{28}$H$_{31}$NO$_4$Na 468.2145, found 468.2142.

Example 4: (4R,5R,6R)-4,5-bis(benzyloxy)-6-((benzyloxy)methyl)-1-ethylpiperidin-2-one. (5a)

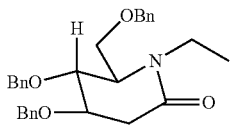

Colorless oil, $C_{29}H_{33}NO_4$, $R_f$ 0.53 (EtOAc-petroleum ether, 1:1); $[\alpha]^{25}_D$ −10.84 (c 1.11, $CHCl_3$); IR ($CHCl_3$): $\nu_{max}$ 3400, 3088, 3065, 3009, 2921, 2853, 1724, 1640, 1455, 1216, 1102, 1027, 756, 698, 667 $cm^{-1}$; 14 h; yield 19%. Flash chromatography elution with 15-25% EtOAc-petroleum ether; $^1H$ NMR (500 MHz, CHLOROFORM-d) $\delta_H$=7.38-7.22 (m, 15H), 4.71-4.63 (m, 1H), 4.63-4.53 (m, 2H), 4.53-4.46 (m, 1H), 4.43 (s, 2H), 3.97-3.91 (m, 1H), 3.87-3.74 (m, 2H), 3.73-3.65 (m, 1H), 3.63-3.57 (m, 1H), 3.55 (dd, J=4.0, 9.2 Hz, 1H), 3.06 (qd, J=13.7, 7.0 Hz, 1H), 2.78 (dd, J=5.0, 16.9 Hz, 1H), 2.50 (dd, J=6.9, 16.9 Hz, 1H), 1.10 (t, J=7.0 Hz, 3H); $^{13}C$ NMR (125 MHz, CHLOROFORM-d) $\delta_C$=168.0, 137.9, 137.9, 137.7, 128.5, 127.9, 127.8, 127.8, 127.7, 127.6, 75.5, 75.4, 73.3, 72.4, 71.3, 69.2, 60.4, 40.4, 35.0, 12.7; ESI-MS: m/z 482.26.16 $(M+Na)^+$; HRMS: m/z calcd for $C_{29}H_{33}NO_4Na$ 482.2302, found 482.2299.

Example 5: (4R,5S,6R)-4,5-bis(benzyloxy)-6-((benzyloxy)methyl)-1-ethylpiperidin-2-one. (6a)

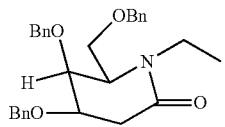

6a

Colorless oil, $C_{29}H_{33}NO_4$, $R_f$=0.49 (EtOAc-petroleum ether, 7:3); $[\alpha]^{25}_D$ +6.23 (c 0.68, $CHCl_3$); IR ($CHCl_3$): $\nu_{max}$ 3401, 3088, 3064, 3008, 2921, 2854, 1724, 1641, 1455, 1215, 1102, 1028, 756, 698, 667 $cm^{-1}$; 69 h; yield 13%. Flash chromatography elution with 20-35% EtOAc-petroleum ether; $^1H$ NMR (500 MHz, CHLOROFORM-d) $\delta_H$=7.36-7.27 (m, 15H), 4.77 (d, J=11.6 Hz, 1H), 4.65-4.56 (m, 3H), 4.48 (s, 2H), 4.04-3.98 (m, 2H), 3.86 (t, J=5.3 Hz, 1H), 3.80-3.69 (m, 3H), 3.33 (qd, J=7.0, 13.7 Hz, 1H), 2.81 (dd, J=6.4, 17.4 Hz, 1H), 2.60 (dd, J=5.2, 17.4 Hz, 1H), 1.09 (t, J=7.0 Hz, 3H); $^{13}C$ NMR (125 MHz, CHLOROFORM-d) $\delta_C$=167.5, 138.1, 138.0, 137.9, 128.4, 127.8, 127.8, 127.7, 127.7, 127.6, 127.4, 74.6, 73.6, 73.4, 72.7, 71.4, 71.4, 58.6, 40.5, 35.7, 12.8; ESI-MS: m/z 482.24 $(M+Na)^+$; HRMS: m/z calcd for $C_{29}H_{34}NO_4$ 460.2482, found 460.2481.

Example 6: (4R,5R,6R)-4,5-bis(benzyloxy)-6-((benzyloxy)methyl)-1-propyl piperidine-2-one. (7a)

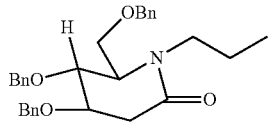

7a

Colorless oil, $C_{30}H_{35}NO_4$, $R_f$ 0.7 (EtOAc-petroleum ether, 1:1); $[\alpha]^{25}_D$ −7.94 (c 0.85 $CHCl_3$); IR ($CHCl_3$): $\nu_{max}$ 3401, 3086, 3065, 3008, 2921, 2853, 1724, 1640, 1456, 1215, 1102, 1027, 756, 698, 667 $cm^{-1}$; 17 h; Yield 7%. Flash chromatography elution with 10-25% EtOAc-petroleum ether; $^1H$ NMR (400 MHz, CHLOROFORM-d) $\delta_H$=7.38-7.26 (m, 15H), 4.72-4.64 (m, 1H), 4.64-4.48 (m, 3H), 4.48-4.39 (m, 2H), 3.95 (dd, J=3.2, 5.6 Hz, 1H), 3.90-3.75 (m, 2H), 3.71-3.64 (m, 1H), 3.64-3.58 (m, 1H), 3.56-3.50 (m, 1H), 2.92-2.84 (m, 1H), 2.84-2.73 (m, 1H), 2.55-2.46 (m, 1H), 1.62-1.54 (m, 2H), 0.87 (d, J=7.3 Hz, 3H); $^{13}C$ NMR (100 MHz, CHLOROFORM-d) $\delta_C$=168.3, 137.9, 137.9, 137.7, 128.5, 127.8, 127.8, 127.7, 127.5, 75.7, 75.5, 73.3, 72.4, 71.3, 69.1, 60.5, 46.9, 35.0, 20.6, 11.2; ESI-MS: m/z 474.1 $(M+H)^+$; HRMS: m/z calcd for $C_{30}H_{35}NO_4$ 474.2639 found 474.2641.

Example 7: (4R,5S,6R)-4,5-bis(benzyloxy)-6-((benzyloxy)methyl)-1-propylpiperidin-2-one. (8a)

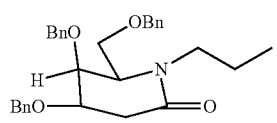

8a

Colorless oil, $C_{30}H_{35}NO_4$, $R_f$ 0.47 (EtOAc-petroleum ether, 7:3); $[\alpha]^{25}_D$ +3.11 (c 1.2, $CHCl_3$); IR ($CHCl_3$): $\nu_{max}$ 3400, 3088, 3065, 3009, 2922, 2855, 1724, 1640, 1456, 1218, 1102, 1027, 756, 698, 667 $cm^{-1}$, $cm^{-1}$; 5 d, yield 22%. Flash chromatography elution with 20-30% EtOAc-petroleum ether; $^1H$ NMR (500 MHz, CHLOROFORM-d) $\delta_H$=7.42-7.19 (m, 16H), 4.76 (d, J=11.6 Hz, 1H), 4.66-4.55 (m, 3H), 4.52-4.41 (m, 2H), 4.06-3.96 (m, 2H), 3.87 (t, J=4.9 Hz, 1H), 3.80-3.67 (m, 3H), 3.21-3.12 (m, 1H), 2.81 (dd, J=17.4, 6.4 Hz, 1H), 2.61 (dd, J=17.4, 4.9, Hz 1H), 1.67-1.53 (m, 2H), 0.83 (t, J=7.5 Hz, 3H); $^{13}C$ NMR (125 MHz, CHLOROFORM-d) $\delta_C$=167.6, 138.1, 138.0, 137.9, 128.4, 127.8, 127.7, 127.7, 127.7, 127.6, 127.4, 74.6, 73.6, 73.3, 72.6, 71.5, 71.4, 58.7, 47.1, 35.7, 20.5, 11.3; ESI-MS: m/z 474.2 $(M+Na)^+$; HRMS: m/z calcd for $C_{30}H_{35}NO_4Na$ 474.2639, found 474.2638.

Example 8: (4R,5R,6R)-4,5-bis(benzyloxy)-6-((benzyloxy)methyl)-1-butylpiperidin-2-one. (9a)

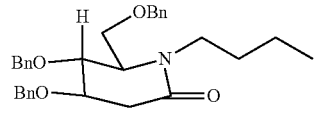

9a

Colorless oil, $C_{31}H_{37}NO_4$, $R_f$ 0.53 (EtOAc-petroleum ether, 1:1); $[\alpha]^{25}_D$ −18.5 (c 1.34, $CHCl_3$); IR ($CHCl_3$): $\nu_{max}$ 3396, 3088, 3064, 3030, 3007, 2958, 2929, 2869, 1723, 1641, 1454, 1266, 1099, 1074, 754, 698 $cm^{-1}$; 22 h, yield 25%. Flash chromatography Elution with 10-20% EtOAc-petroleum ether; $^1H$ NMR (500 MHz, CHLOROFORM-d) $\delta_H$=7.38-7.20 (m, 15H), 4.71-4.64 (m, 1H), 4.62-4.53 (m, 2H), 4.53-4.46 (m, 1H), 4.46-4.38 (m, 2H), 3.95 (dd, J=3.2, 5.0 Hz, 1H), 3.87-3.78 (m, 2H), 3.71-3.63 (m, 1H), 3.62-3.57 (m, 1H), 3.53 (dd, J=4.0, 9.5 Hz, 1H), 2.89 (ddd, J=5.3, 8.9, 13.6 Hz, 1H), 2.78 (dd, J=4.9, 16.8 Hz, 1H), 2.50 (dd, J=7.3, 16.8 Hz, 1H), 1.57-1.40 (m, 2H), 1.34-1.27 (m, 2H), 0.88 (t, J=7.2 Hz, 3H); $^{13}C$ NMR (125 MHz, CHLOROFORM-d) $\delta_C$=168.1, 138.0, 137.9, 137.7, 128.5, 127.8, 127.8, 127.7, 127.6, 127.6, 75.8, 75.6, 73.3, 72.4, 71.3, 69.1, 60.5, 45.0, 35.1, 29.5, 20.1, 13.9; ESI-MS: m/z 510.13 $(M+Na)^+$; HRMS: m/z calcd for $C_{31}H_{38}NO_4$ 488.2795, found 488.2792.

Example 9: (4R,5S,6R)-4,5-bis(benzyloxy)-6-((benzyloxy)methyl)-1-butylpiperidin-2-one. (10a)

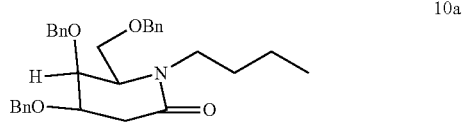 [SMILES: CCCCN1C(=O)CC(OCc2ccccc2)C(OCc2ccccc2)C1COCc1ccccc1]

10a

Colorless oil, C$_{31}$H$_{37}$NO$_4$, R$_f$ 0.56 (EtOAc-petroleum ether, 7:3); [α]$^{25}_D$ +3.03 (c 0.86, CHCl$_3$); IR (CHCl$_3$): ν$_{max}$ 3395, 3088, 3063, 3029, 3006, 2957, 2928, 2868, 1721, 1640, 1454, 1263, 1097, 1074, 754, 697 cm$^{-1}$; 69 h, yield 30%. Flash chromatography elution with 20-35% EtOAc-petroleum ether; $^1$H NMR (500 MHz, CHLOROFORM-d) δ$_H$=7.35-7.26 (m, 15H), 4.76 (d, J=11.6 Hz, 1H), 4.64-4.56 (m, 3H), 4.51-4.45 (m, 2H), 4.02 (dd, J=3.4, 9.5 Hz, 1H), 3.99 (dd, J=1.7, 4.4 Hz, 1H), 3.89-3.85 (m, 1H), 3.80-3.72 (m, 3H), 3.22-3.14 (m, 1H), 2.81 (dd, J=6.1, 17.4 Hz, 1H), 2.61 (dd, J=5.2, 17.4 Hz, 1H), 1.58-1.50 (m, 1H), 1.44-1.36 (m, 1H), 1.31-1.26 (m, 2H), 0.88 (t, J=7.2 Hz, 3H); $^{13}$C NMR (125 MHz, CHLOROFORM-d) δ$_C$=167.6, 138.1, 138.0, 138.0, 128.4, 127.8, 127.7, 127.6, 127.6, 127.4, 74.6, 73.6, 73.3, 72.6, 71.4, 71.4, 58.7, 45.3, 35.8, 29.4, 20.2, 13.9; ESI-MS: m/z 510.35 (M+Na)$^+$; HRMS: m/z calcd for C$_{31}$H$_{37}$NO$_4$Na 510.2615, found 510.2613.

Example 10: (4R,5R,6R)-1-benzyl-4,5-bis(benzyloxy)-6-((benzyloxy)methyl) piperidin-2-one. (11a)

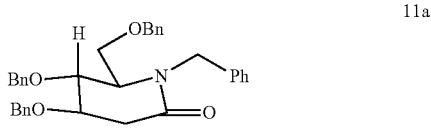 [SMILES: O=C1CC(OCc2ccccc2)C(OCc2ccccc2)C(COCc2ccccc2)N1Cc1ccccc1]

11a

Flash chromatography: elution with 15-25% EtOAc-petroleum ether; yield 42%; colorless oil; R$_f$ 0.7 (EtOAc-petroleum ether, 7:3); [α]$^{25}_D$ −7.56 (c 1.33 CHCl$_3$); IR (CHCl$_3$): ν$_{max}$ 3444, 3088, 3065, 3030, 2925, 2855, 1643, 1453, 1248, 1099, 756, 698, 666 cm$^{-1}$; $^1$H NMR (500 MHz, CHLOROFORM-d) δ$_H$=7.35-7.13 (m, 20H), 5.32 (d, J=15.4 Hz, 1H), 4.66-4.55 (m, 1H), 4.54-4.44 (m, 2H), 4.41-4.32 (m, 3H), 4.10 (d, J=15.2 Hz, 1H), 3.95-3.91 (m, 1H), 3.88 (q, J=5.5 Hz, 1H), 3.69-3.64 (m, 1H), 3.62-3.58 (m, 1H), 3.58-3.53 (m, 1H), 2.91 (dd, J=5.1, 17.1 Hz, 1H), 2.63 (dd, J=6.4, 17.1 Hz, 1H); $^{13}$C NMR (126 MHz, CHLOROFORM-d) δ$_C$=168.5, 137.8, 137.8, 137.7, 137.1, 128.6, 128.5, 128.5, 128.4, 128.4, 127.9, 127.8, 127.8, 127.8, 127.7, 127.7, 127.5, 127.5, 127.2, 75.3, 75.2, 73.2, 72.1, 71.4, 69.1, 58.9, 47.7, 35.0; ESI-MS: m/z 544.28 (M+Na)$^+$; HRMS: m/z calcd for C$_{34}$H$_{35}$NO$_4$Na 544.2458, found 544.2458.

Example 11: (4R,5R,6R)-1-allyl-4,5-bis(benzyloxy)-6-((benzyloxy)methyl) piperidin-2-one. (12a)

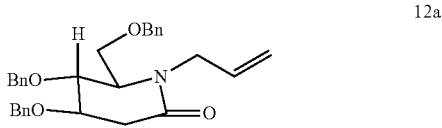

12a

Flash chromatography: elution with 20-25% EtOAc-petroleum ether; yield 26%; colorless oil, R$_f$ 0.59 (EtOAc-petroleum ether, 1:1); [α]$^{25}_D$ −2.72 (c 0.71 CHCl$_3$); IR (CHCl$_3$): ν$_{max}$ 3446, 3086, 3064, 3030, 3007, 2922, 2855, 1650, 1456, 1259, 1206, 1099, 1028, 739, 699 cm$^{-1}$; 1H NMR (200 MHz, CHLOROFORM-d) δ$_H$=7.43-7.25 (m, 15H), 5.89-5.61 (m, 1H), 5.24-5.12 (m, 1H), 5.12-5.06 (m, 1H), 4.75-4.44 (m, 6H), 4.41 (s, 2H), 4.02-3.93 (m, 1H), 3.92-3.79 (m, 1H), 3.73-3.48 (m, 4H), 2.82 (dd, J=5.0, 17.0 Hz, 1H), 2.54 (dd, J=6.6, 17.1 Hz, 1H); $^{13}$C NMR (100 MHz, CHLOROFORM-d) δ$_C$=168.3, 137.9, 137.9, 137.8, 133.3, 128.5, 128.0, 127.9, 127.8, 127.6, 117.2, 75.4, 73.2, 72.5, 71.4, 68.9, 59.8, 47.4, 35.0; ESI-MS: m/z 494.25 (M+Na)$^+$; HRMS: m/z calcd for C$_{30}$H$_{33}$NO$_4$Na 494.2302, found 494.2296.

Example 12: (4R,5S,6R)-1-allyl-4,5-bis(benzyloxy)-6-((benzyloxy)methyl) piperidin-2-one. (13a)

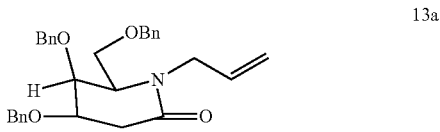 [SMILES: C=CCN1C(=O)CC(OCc2ccccc2)C(OCc2ccccc2)C1COCc1ccccc1]

13a

Colorless oil, C$_{30}$H$_{33}$NO$_4$, R$_f$ 0.45 (EtOAc-petroleum ether, 7:3); [α]$^{25}_D$+20.73 (c 1.27, CHCl$_3$); IR (CHCl$_3$): ν$_{max}$ 3445, 3086, 3063, 3032, 3006, 2924, 2852, 1650, 1456, 1257, 1204, 1097, 1028, 739, 699 cm$^{-1}$; 10 h, yield 71%. Flash chromatography Elution with 10-20% EtOAc-petroleum ether; $^1$H NMR (400 MHz, CHLOROFORM-d) δ$_H$=7.36-7.23 (m, 15H), 5.80-5.67 (m, 1H), 5.16-5.03 (m, 2H), 4.76 (d, J=11.7 Hz, 1H), 4.68-4.54 (m, 3H), 4.48-4.38 (m, 3H), 4.06-3.91 (m, 2H), 3.91-3.72 (m, 4H), 2.85 (dd, J=6.5, 17.5 Hz, 1H), 2.63 (dd, J=5.1, 17.6 Hz, 1H); $^{13}$C NMR (100 MHz, CHLOROFORM-d) δ$_C$=167.7, 138.1, 138.0, 138.0, 133.1, 128.4, 127.8, 127.7, 127.7, 127.6, 127.4, 116.9, 74.5, 73.8, 73.3, 72.7, 71.4, 71.1, 58.3, 47.3, 35.6; ESI-MS: m/z 494.27 (M+Na)$^+$; HRMS: m/z calcd for C$_{30}$H$_{34}$NO$_4$ 472.2482, found 472.2482.

Example 13: (4R,5R,6R)-4,5-bis(benzyloxy)-1-(2-(benzyloxy)ethyl)-6-((benzyloxy)methyl) piperidin-2-one. (14a)

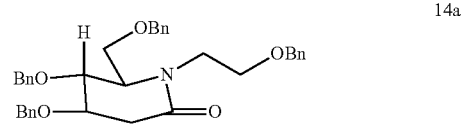

14a

Colorless oil, C$_{36}$H$_{39}$NO$_5$, R$_f$ 0.47 (EtOAc-petroleum ether, 1:1); [α]$^{25}_D$ −12.45 (c 0.79 CHCl$_3$); IR (CHCl$_3$): ν$_{max}$ 3409, 3087, 2922, 2857, 2360, 1722, 1647, 1454, 1365, 1271, 1100, 1028, 738, 698 cm$^{-1}$; 8 h, yield 12%. Flash chromatography Elution with 20-25% EtOAc-petroleum ether; $^1$H NMR (500 MHz, CHLOROFORM-d) δ$_H$=7.33-7.22 (m, 20H), 4.64-4.60 (m, 1H), 4.59-4.53 (m, 2H), 4.51-4.46 (m, 1H), 4.44 (d, J=3.7 Hz, 2H), 4.39 (s, 2H), 3.99-3.92 (m, 2H), 3.88-3.81 (m, 2H), 3.70 (dd, J=6.3, 9.9 Hz, 1H), 3.67-3.63 (m, 1H), 3.60 (td, J=5.0, 10.2 Hz, 2H), 3.32 (ddd, J=5.2, 7.3, 14.0 Hz, 1H), 2.79 (dd, J=5.2, 16.8 Hz, 1H), 2.52 (dd, J=6.9, 16.9 Hz, 1H); $^{13}$C NMR (126 MHz, CHLOROFORM-d) $\delta_C$=168.6, 138.2, 138.0, 137.9, 137.8, 128.4, 128.4, 128.3, 127.8, 127.7, 127.6, 127.5, 75.5, 75.4, 73.2, 73.1, 72.1, 71.3, 69.2, 68.6, 61.4, 45.5, 35.1; ESI-MS: m/z 588.2 (M+Na)$^+$; HRMS: m/z calcd for $C_{36}H_{40}NO_5$ 566.2901, found 566.2900.

Example 14: (4R,5S,6R)-4,5-bis(benzyloxy)-1-(2-(benzyloxy)ethyl)-6-((benzyloxy) methyl)piperidin-2-one. (15a)

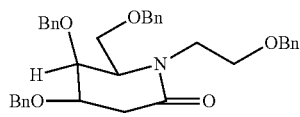

15a

Colorless oil, $C_{36}H_{39}NO_5$, $R_f$ 0.62 (EtOAc-petroleum ether, 7:3); $[\alpha]^{25}_D$ +13.78 (c 0.81, CHCl$_3$); IR (CHCl$_3$): $v_{max}$ 3408, 3087, 2924, 2857, 2360, 1722, 1646, 1455, 1365, 1270, 1100, 1025, 738, 698 cm$^{-1}$; 62 h, yield 12%. Flash chromatography Elution with 20-35% EtOAc-petroleum ether; 1H NMR (500 MHz, CHLOROFORM-d) $\delta_H$=7.32-7.25 (m, 20H), 4.64-4.54 (m, 4H), 4.48-4.34 (m, 5H), 4.07-4.00 (m, 1H), 3.99-3.94 (m, 2H), 3.89-3.84 (m, 2H), 3.72-3.65 (m, 1H), 3.62-3.50 (m, 2H), 2.78 (dd, J=17.5, 5.6 Hz, 1H), 2.60 (dd, J=17.5 Hz, 5.3, 1H); $^{13}$C NMR (125 MHz, CHLOROFORM-d) $\delta_C$=168.0, 138.4, 138.2, 138.1, 138.1, 128.4, 128.4, 127.7, 127.7, 127.6, 127.5, 127.4, 74.8, 73.6, 73.2, 72.9, 72.4, 71.8, 71.6, 68.3, 59.6, 45.4, 36.0; ESI-MS: m/z 588.68 (M+Na)$^+$; HRMS: m/z calcd for $C_{36}H_{39}NO_5Na$ 588.2720, found 588.2722.

Example 15: Synthesis of N-Alkyl-α,β-Unsaturated Glycolactam (16b-28b)

To a solution of glycolactam (50 mg, 0.12 mmol) in 8 ml DMF at 0° C. was added NaH (60% dispersion in oil, 15 mg, 5.3 eq) and stirred at 0° C. for 10 min. Alkyl halide RX (2-5 eq) was added and stirred at 0° C. till complete consumption of starting material with periodic TLC check. Ethyl acetate (10 ml) was added followed by cold sat. NH$_4$Cl solution dropwise with vigorous stirring. The aq layer was extracted with ethyl acetate (4×10 ml), dried, concentrated and residual nonvolatile solvent was removed by co-distillation with toluene under reduced pressure with water bath temperature not exceeding 50° C., crude was then subjected to flash chromatography.

Example 16: (5S,6R)-5-(benzyloxy)-6-((benzyloxy) methyl)-1-methyl-5,6-dihydropyridin-2(1H)-one. (16b)

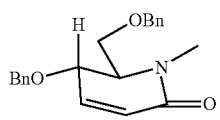

16b

Colorless oil, $C_{21}H_{23}NO_3$, $R_f$ 0.45 (EtOAc-petroleum ether, 1:1); $[\alpha]^{25}_D$ +179.1280 (c 1.0, CHCl$_3$); IR (CHCl$_3$): $v_{max}$ 3384, 3016, 2961, 2931, 2871, 2361, 1721, 1664, 1611, 1454, 1269, 1216, 1069, 768, 712, 668 cm$^{-1}$; 29 h, yield 82%. Flash chromatography Elution with 15-25% EtOAc-petroleum ether; $^1$H NMR (500 MHz, CHLOROFORM-d) $\delta_H$ 7.37-7.24 (m, 10H), 6.42 (ddd, J=9.7, 5.5, 0.9 Hz, 1H), 6.07 (d, J=10.1 Hz, 1H), 4.58 (s, 2H), 4.50 (d, J=11.9 Hz, 1H), 4.44 (d, J=11.9 Hz, 1H), 4.13 (dd, J=0.9, 5.5 Hz, 1H), 3.79-3.74 (m, 1H), 3.53 (dd, J=4.9, 9.5 Hz, 1H), 3.31 (t, J=9.2 Hz, 1H), 3.01 (s, 3H); $^{13}$C NMR (125 MHz, CHLOROFORM-d) $\delta_C$ 162.5, 137.8, 137.4, 134.4, 128.5, 128.5, 128.0, 128.0, 127.9, 127.8, 127.6, 73.4, 70.4, 68.6, 67.9, 62.0, 34.0; ESI-MS: m/z 360.09 (M+Na)$^+$; HRMS: m/z calcd for $C_{21}H_{24}NO_3Na$ 338.1751, found 338.1749.

Example 17: (5R,6R)-5-(benzyloxy)-6-((benzyloxy) methyl)-1-methyl-5,6-dihydropyridin-2(1H)-one. (17b)

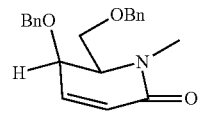

17b

Colorless oil, $C_{21}H_{22}NO_3$, $C_{21}H_{23}NO_3$, $R_f$ 0.47 (EtOAc-petroleum ether, 1:1); $[\alpha]^{25}_D$ +65.32 (c 1.06, CHCl$_3$); IR (CHCl$_3$): $v_{max}$ 3383, 3015, 2961, 2931, 2873, 2361, 1720, 1663, 1611, 1454, 1269, 1216, 1069, 768, 712, 668 cm$^{-1}$; 34 h, yield 54%. Flash chromatography Elution with 10-20% EtOAc-petroleum ether; $^1$H NMR (400 MHz, CHLOROFORM-d) $\delta_H$=7.40-7.24 (m, 10H), 6.38 (d, J=10.1 Hz, 1H), 5.83 (dd, J=10.1, 2.4 Hz, 1H), 4.65 (dd, J=2.3, 3.5 Hz, 1H), 4.63-4.54 (m, 2H), 4.54-4.44 (m, 2H), 3.94-3.87 (m, 1H), 3.84-3.75 (m, 2H), 3.11 (s, 3H); $^{13}$C NMR (100 MHz, CHLOROFORM-d) $\delta_C$=163.5, 140.0, 138.0, 137.2, 128.6, 128.4, 128.1, 127.7, 127.5, 124.5, 73.6, 72.9, 71.6, 68.8, 61.1, 35.4; ESI-MS: m/z 360.01 (M+Na)$^+$; HRMS: m/z calcd for $C_{21}H_{23}NO_3$ 338.1751, found 338.1747.

Example 18: (5S,6R)-5-(benzyloxy)-6-((benzyloxy) methyl)-1-ethyl-5,6-dihydropyridin-2(1H)-one. (18b)

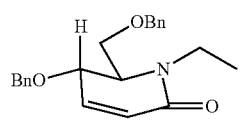

18b

Colorless oil, $C_{22}H_{25}NO_3$, $R_f$ 0.32 (EtOAc-petroleum ether, 1:1); $[\alpha]^{25}_D$ +140.63 (c 0.89, CHCl$_3$); IR (CHCl$_3$): $v_{max}$ 3446, 3064, 3006, 2925, 2855, 1668, 1611, 1471, 1455, 1217, 1090, 1070, 1027, 755, 699 cm$^{-1}$; 12 h, yield 44%. Flash chromatography elution with 20-25% EtOAc-petroleum ether; $^1$H NMR (500 MHz, CHLOROFORM-d) $\delta_H$=7.38-7.25 (m, 10H), 6.41 (dd, J=5.8, 8.9 Hz, 1H), 6.07 (d, J=9.8 Hz, 1H), 4.65-4.54 (m, 2H), 4.52-4.41 (m, 2H), 4.13 (d, J=5.2 Hz, 1H), 4.05-3.95 (m, 1H), 3.82 (dd, J=4.4, 8.7 Hz, 1H), 3.50 (dd, J=4.6, 9.5 Hz, 1H), 3.32 (t, J=9.3 Hz, 1H), 2.89 (qd, J=7.0, 13.7 Hz, 1H), 1.16 (t, J=7.0 Hz, 3H); $^{13}$C NMR (125 MHz, CHLOROFORM-d) $\delta_C$=161.9, 137.9, 137.5, 134.2, 128.6, 128.5, 128.5, 128.0, 127.9, 127.7, 127.6, 73.4, 70.4, 68.4, 59.0, 40.7, 12.9; ESI-MS: m/z 374.11 (M+Na)⁺; HRMS: m/z calcd for C₂₂H₂₆NO₃ 352.1907, found 352.1906.

Example 19: (5R,6R)-5-(benzyloxy)-6-((benzyloxy)methyl)-1-ethyl-5,6-dihydropyridin-2(1H)-one. (19b)

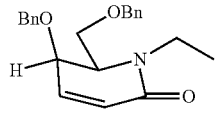

Colorless oil, C₂₂H₂₅NO₃, R_f 0.57 (EtOAc-petroleum ether, 7:3); [α]²⁵_D +32.66 (c 1.0, CHCl₃); IR (CHCl₃): ν_max 3446, 3063, 3006, 2924, 2853, 1668, 1611, 1473, 1453, 1214, 1089, 1070, 1028, 755, 699 cm⁻¹; 34 h, yield 49%. Flash chromatography elution with 10-20% EtOAc-petroleum ether; ¹H NMR (500 MHz, CHLOROFORM-d) δ_H=7.50-7.26 (m, 10H), 6.39 (d, J=9.9 Hz, 1H), 5.85 (dd, J=2.3, 9.9 Hz, 1H), 4.69-4.64 (m, 1H), 4.64-4.58 (m, 2H), 4.56-4.47 (m, 2H), 4.09 (qd, J=7.2, 13.9 Hz, 1H), 3.95 (dd, J=9.5, 3.1 Hz, 1H), 3.90-3.83 (m, 1H), 3.81-3.73 (m, 1H), 3.12 (qd, J=13.9, 6.9 Hz, 1H), 1.18 (t, J=7.1 Hz, 3H); ¹³C NMR (125 MHz, CHLOROFORM-d) δ_C=162.8, 140.0, 138.0, 137.2, 128.6, 128.4, 128.1, 127.8, 127.7, 127.5, 124.7, 73.7, 73.6, 71.6, 69.0, 58.0, 41.7, 13.8; ESI-MS: m/z 374.03 (M+Na)⁺; HRMS: m/z calcd for C₂₂H₂₆NO₃ 352.1907, found 352.1904.

Example 20: (5S,6R)-5-(benzyloxy)-6-((benzyloxy)methyl)-1-propyl-5,6-dihydropyridin-2(1H)-one. (20b)

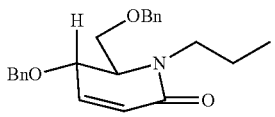

Colorless oil, C₂₃H₂₇NO₃, R_f 0.46 (EtOAc-petroleum ether, 7:3); [α]²⁵_D +130.42 (c 1.05, CHCl₃; IR (CHCl₃): ν_max 3384, 3015, 2963, 2930, 2870, 2361, 1721, 1664, 1611, 1452, 1269, 1216, 1069, 768, 712, 668 cm⁻¹, 50 h, yield 50% Flash chromatography elution with 10-20% EtOAc-petroleum ether; ¹H NMR (500 MHz, CHLOROFORM-d) δ_H 7.36-7.26 (m, 10H), 6.41 (ddd, J=9.7, 5.6, 1.2, Hz, 1H), 6.06 (d, J=9.8 Hz, 1H), 4.62 (d, J=11.9 Hz, 1H), 4.57 (d, J=11.9 Hz, 1H), 4.49 (d, J=11.9 Hz, 1H), 4.44 (d, J=11.9 Hz, 1H), 4.13-4.10 (m, 1H), 3.97 (td, J=7.6, 13.4 Hz, 1H), 3.82 (dd, J=4.6, 9.2 Hz, 1H), 3.49 (dd, J=4.7, 9.6 Hz, 1H), 3.31 (t, J=9.5 Hz, 1H), 2.73 (td, J=6.9, 13.7 Hz, 1H), 1.59 (sxt, J=7.3 Hz, 2H), 0.92 (t, J=7.3 Hz, 3H); ¹³C NMR (125 MHz, CHLOROFORM-d) δ_C 162.2, 137.9, 137.5, 134.1, 128.5, 128.5, 128.0, 127.9, 127.7, 127.6, 73.4, 70.5, 68.5, 68.2, 59.1, 47.3, 21.1, 11.2; ESI-MS: m/z 388.2 (M+H)⁺; HRMS: m/z calcd for C₂₃H₂₈NO₃ 366.2064, found 366.2063.

Example 21: (5R,6R)-5-(benzyloxy)-6-((benzyloxy)methyl)-1-propyl-5,6-dihydropyridin-2(1H)-one. (21b)

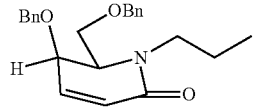

Colorless oil, C₂₃H₂₇NO₃, R_f 0.63 (EtOAc-petroleum ether, 7:3); [α]²⁵_D +29.37 (c 1.05 CHCl₃); IR (CHCl₃): ν_max 3402, 3083, 3066, 3006, 2923, 2854, 1724, 1640, 145, 1216, 1103, 1027, 756, 698, 667 cm⁻¹; 20 h, yield 50%. Flash chromatography elution with 20-35% EtOAc-petroleum ether; ¹H NMR (500 MHz, CHLOROFORM-d) δ_H=7.39-7.24 (m, 10H), 6.35 (d, J=10.1 Hz, 1H), 5.81 (dd, J=2.4, 10.1 Hz, 1H), 4.65-4.54 (m, 3H), 4.52-4.44 (m, 2H), 4.04 (td, J=7.3, 14.0 Hz, 1H), 3.91 (dd, J=3.4, 9.8 Hz, 1H), 3.84-3.77 (m, 1H), 3.77-3.70 (m, 1H), 2.98-2.89 (m, 1H), 1.62-1.52 (m, 2H), 0.89 (t, J=7.3 Hz, 3H); ¹³C NMR (125 MHz, CHLOROFORM-d) δ_C=163.0, 140.0, 138.0, 137.2, 128.6, 128.4, 128.1, 127.8, 127.7, 127.5, 124.7, 73.6, 73.5, 71.6, 69.0, 58.5, 48.5, 21.7, 11.3; ESI-MS: m/z 366.2 (M+H)⁺; HRMS: m/z calcd for C₂₃H₂₈NO₃ 366.2064, found 366.2062.

Example 22: (5S,6R)-5-(benzyloxy)-6-((benzyloxy)methyl)-1-butyl-5,6-dihydropyridin-2(1H)-one. (22b)

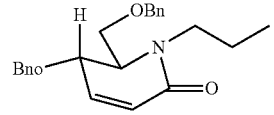

Colorless oil, C₂₄H₂₉NO₃, R_f 0.41 (EtOAc-petroleum ether, 1:1); [α]²⁵_D +133.4359 (c 1.17 CHCl₃); IR (CHCl₃): ν_max 3384, 3017, 2962, 2931, 2872, 2361, 1721, 1664, 1611, 1452, 1269, 1216, 1069, 768, 712, 668 cm⁻¹; 4 h, yield 73%. Flash chromatography Elution with 20-35% EtOAc-petroleum ether; ¹H NMR (500 MHz, CHLOROFORM-d) δ_H=7.40-7.24 (m, 10H), 6.42 (ddd, J=1.5, 5.6, 9.7 Hz, 1H), 6.06 (d, J=9.7 Hz, 1H), 4.65-4.35 (m, 4H), 4.18-4.05 (m, 1H), 4.05-3.91 (m, 1H), 3.82 (tdd, J=1.3, 4.6, 9.4 Hz, 1H), 3.50 (dd, J=4.7, 9.5 Hz, 1H), 3.30 (t, J=9.5 Hz, 1H), 2.75 (td, J=6.8, 13.5 Hz, 1H), 1.60-1.44 (m, 2H), 1.42-1.29 (m, 2H), 0.94-0.84 (m, 3H); ¹³C NMR (100 MHz, CHLOROFORM-d) δ_C=162.2, 137.9, 137.5, 134.1, 128.6, 128.6, 128.0, 127.9, 127.8, 127.7, 73.4, 70.5, 68.6, 68.2, 59.1, 45.5, 30.1, 20.0, 14.0; ESI-MS: m/z 402.09 (M+Na)⁺; HRMS: m/z calcd for C₂₄H₃₀NO₃ 380.2220, found 380.2217.

Example 23: (5R,6R)-5-(benzyloxy)-6-((benzyloxy)methyl)-1-butyl-5,6-dihydropyridin-2(1H)-one. (23b)

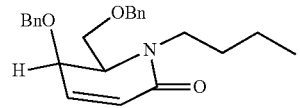

Colorless oil, $C_{24}H_{29}NO_3$, $R_f$ 0.47 (EtOAc-petroleum ether, 1:1); $[\alpha]^{25}_D$ +36.23 (c 1.10, $CHCl_3$); IR ($CHCl_3$): $\nu_{max}$ 3382, 3016, 2961, 2931, 2872, 2361, 1720, 1665, 1612, 1451, 1268, 1215, 1068, 767, 714, 665 cm$^{-1}$; 24 h, yield 50%. Flash chromatography elution with 10-20% EtOAc-petroleum ether; $^1$H NMR (500 MHz, CHLOROFORM-d) $\delta_H$ 7.40-7.23 (m, 10H), 6.35 (d, J=10.1 Hz, 1H), 5.81 (dd, J=10.1, 2.4 Hz, 1H), 4.65-4.61 (m, 1H), 4.61-4.55 (m, 2H), 4.52-4.44 (m, 2H), 4.11-4.03 (m, 1H), 3.91 (dd, J=9.6, 3.2 Hz, 1H), 3.83-3.77 (m, 1H), 3.76-3.71 (m, 1H), 3.01-2.92 (m, 1H), 1.52 (quin, J=7.5 Hz, 2H), 1.33-1.28 (m, 2H), 0.91 (t, J=7.3 Hz, 3H); $^{13}$C NMR (125 MHz, CHLOROFORM-d) $\delta_C$ 163.0, 140.0, 138.0, 137.2, 128.6, 128.4, 128.1, 127.8, 127.7, 127.5, 124.7, 73.6, 73.5, 71.6, 69.0, 58.4, 46.6, 30.7, 20.1, 13.9; ESI-MS: m/z 402.11 (M+Na)$^+$; HRMS: m/z calcd for $C_{24}H_{30}NO_3$ 380.2220, found 380.2220.

Example 24: (5S,6R)-1-benzyl-5-(benzyloxy)-6-((benzyloxy)methyl)-5,6-dihydropyridin-2(1H)-one. (24b)

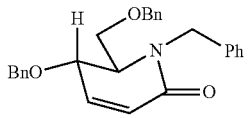

24b

Colorless oil, $C_{27}H_{27}NO_3$, $R_f$ 0.62 (EtOAc-petroleum ether, 7:3); $[\alpha]^{25}_D$ +173.41 (c 1.4, $CHCl_3$); IR ($CHCl_3$): $\nu_{max}$ 3064, 3030, 3007, 2923, 2860, 1721, 1668, 1612, 1495, 1452, 1266, 1094, 754, 699 cm$^{-1}$; 8 h, yield 77%. Flash chromatography elution with 10-15% EtOAc-petroleum ether; $^1$H NMR (500 MHz, CHLOROFORM-d) $\delta_H$ 7.38-7.22 (m, 13H), 7.13 (brs., 2H), 6.48-6.45 (m, 1H), 6.16 (d, J=9.5 Hz, 1H), 5.38 (d, J=15.3 Hz, 1H), 4.44 (d, J=11.9 Hz, 1H), 4.40 (d, J=11.9 Hz, 1H), 4.32 (d, J=11.6 Hz, 1H), 4.28 (d, J=11.6 Hz, 1H), 4.13-4.05 (m, 1H), 4.00 (d, J=15.3 Hz, 1H), 3.83 (brs., 1H), 3.48 (dd, J=3.8, 8.7 Hz, 1H), 3.34 (t, J=9.0 Hz, 1H); $^{13}$C NMR (125 MHz, CHLOROFORM-d) $\delta_C$ 162.5, 137.6, 137.5, 137.0, 134.8, 128.6, 128.5, 128.4, 128.1, 128.1, 128.0, 127.8, 127.6, 127.4, 73.3, 70.2, 68.6, 68.1, 57.4, 48.1; ESI-MS: m/z 436.07 (M+Na)$^+$; HRMS: m/z calcd for $C_{27}H_{27}NO_3Na$ 436.1883, found 436.1880.

Example 25: (5S,6R)-1-allyl-5-(benzyloxy)-6-((benzyloxy)methyl)-5,6-dihydro pyridin-2(1H)-one. (25b)

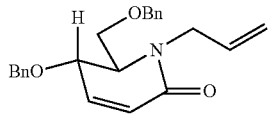

25b

Colorless oil, $C_{23}H_{25}NO_3$, $R_f$ 0.41 (EtOAc-petroleum ether, 1:1); $[\alpha]^{25}_D$ +160.41 (c 1.22 $CHCl_3$); IR ($CHCl_3$): $\nu_{max}$ 3445, 3065, 3012, 2923, 2855, 2361, 2340, 1721, 1668, 1613, 1417, 1217, 1109, 1068, 757, 699 cm$^{-1}$; 26 h, yield 77%. Flash chromatography elution with 20-35% EtOAc-petroleum ether; $^1$H NMR (200 MHz, CHLOROFORM-d) $\delta_H$=7.40-7.21 (m, 10H), 6.44 (ddd, J=1.5, 5.6, 9.8 Hz, 1H), 6.09 (d, J=9.9 Hz, 1H), 5.90-5.66 (m, 1H), 5.37-5.21 (m, 1H), 5.16 (dd, J=1.3, 10.1 Hz, 1H), 4.72-4.62 (m, 1H), 4.61-4.52 (m, 2H), 4.51-4.42 (m, 2H), 4.13 (dd, J=1.4, 5.6 Hz, 1H), 3.88 (tdd, J=1.4, 4.8, 9.1 Hz, 1H), 3.59-3.42 (m, 2H), 3.39-3.24 (m, 1H); $^{13}$C NMR (50 MHz, CHLOROFORM-d) $\delta_C$=162.1, 137.8, 137.5, 134.6, 133.0, 128.5, 128.1, 127.9, 127.9, 127.6, 117.6, 77.7, 77.1, 76.4, 73.3, 70.4, 68.7, 68.2, 58.2, 47.7; ESI-MS: m/z 386.04 (M+Na)$^+$; HRMS: m/z calcd for $C_{23}H_{25}NO_3Na$ 386.1727, found 386.1722.

Example 26: (5R,6R)-1-allyl-5-(benzyloxy)-6-((benzyloxy)methyl)-5,6-dihydro pyridin-2(1H)-one. (26b)

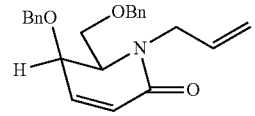

26b

Colorless oil, $R_f$, $C_{23}H_{24}NO_3$, 0.58 (EtOAc-petroleum ether, 1:1); $[\alpha]^{25}_D$ +54.89 (c 1.15, $CHCl_3$); IR ($CHCl_3$): $\nu_{max}$ 3444, 3065, 3013, 2923, 2855, 2362, 2341, 1721, 1668, 1613, 1417, 1215, 1106, 1068, 757, 699 cm$^{-1}$; 8 h, yield 55%. Flash chromatography Elution with 10-20% EtOAc-petroleum ether; $^1$H NMR (500 MHz, CHLOROFORM-d) $\delta_H$=7.40-7.19 (m, 10H), 6.38 (d, J=10.1 Hz, 1H), 5.85 (dd, J=10.1, 2.4 Hz, 1H), 5.78 (dddd, J=4.3, 7.2, 10.2, 17.1 Hz, 1H), 5.23-5.11 (m, 2H), 4.87-4.76 (m, 1H), 4.65-4.52 (m, 3H), 4.52-4.42 (m, 2H), 3.93-3.83 (m, 2H), 3.82-3.74 (m, 1H), 3.59 (dd, J=7.3, 15.6 Hz, 1H); $^{13}$C NMR (125 MHz, CHLOROFORM-d) $\delta_C$=162.8, 140.4, 138.0, 137.1, 133.8, 128.6, 128.4, 128.1, 127.8, 127.7, 127.5, 124.4, 117.2, 73.5, 73.3, 71.7, 68.8, 57.0, 48.5; ESI-MS: m/z 386.07 (M+Na)$^+$; HRMS: m/z calcd for $C_{23}H_{25}NO_3$ 364.1907, found 364.1903.

Example 27: (5S,6R)-5-(benzyloxy)-1-(2-(benzyloxy)ethyl)-6-((benzyloxy) methyl)-5,6-dihydropyridin-2(1H)-one. (27b)

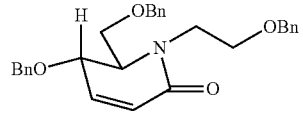

27b

Colorless oil, $C_{29}H_{31}NO_4$, $R_f$ 0.31 (EtOAc-petroleum ether, 1:1); $[\alpha]^{25}_D$ +107.59 (c 1.17, $CHCl_3$); IR ($CHCl_3$): $\nu_{max}$ 3062, 3030, 3006, 2924, 2860, 1669, 1614, 1495, 1456, 1360, 1204, 1101, 1028, 820, 739, 699 cm$^{-1}$; 22 h, yield 47%. Flash chromatography elution with 35-40% EtOAc-petroleum ether; $^1$H NMR (500 MHz, CHLOROFORM-d) $\delta_H$=7.39-7.16 (m, 15H), 6.43 (dd, J=6.6, 9.6 Hz, 1H), 6.07 (d, J=9.8 Hz, 1H), 4.59-4.35 (m, 6H), 4.17-4.00 (m, 3H), 3.74-3.61 (m, 2H), 3.58 (dd, J=4.7, 9.6 Hz, 1H), 3.35-3.18 (m, 2H); $^{13}$C NMR (125 MHz, CHLOROFORM-d) $\delta_C$=162.5, 138.1, 137.9, 137.6, 134.8, 128.4, 128.4, 128.3, 128.1, 127.8, 127.8, 127.7, 127.6, 73.3, 73.2, 70.1, 69.1, 68.4, 68.2, 60.0, 46.2; ESI-MS: m/z 480.16 (M+Na)$^+$; HRMS: m/z calcd for $C_{29}H_{31}NO_4Na$ 480.2145, found 480.2141.

Example 28: (5R,6R)-5-(benzyloxy)-1-(2-(benzyloxy)ethyl)-6-((benzyloxy)methyl)-5,6-dihydropyridin-2(1H)-one. (28b)

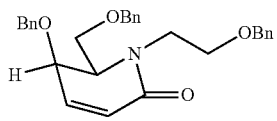

Colorless oil, $C_{29}H_{31}NO_4$, $R_f$ 0.47 (EtOAc-petroleum ether, 7:3); $[\alpha]^{25}_D$ +52.44 (c 0.97 CHCl$_3$); IR (CHCl$_3$): $v_{max}$ 3061, 3029, 3003, 2924, 2861, 1668, 1613, 1497, 1455, 1362, 1208, 1102, 1026, 820, 739, 699 cm$^{-1}$; 60 h, yield 37%. Flash chromatography elution with 20-35% EtOAc-petroleum ether; $^1$H NMR (500 MHz, CHLOROFORM-d) $\delta_H$=7.35-7.20 (m, 15H), 6.35 (d, J=10.1 Hz, 1H), 5.81 (dd, J=2.4, 10.1 Hz, 1H), 4.63-4.57 (m, 1H), 4.52-4.43 (m, 5H), 4.36-4.28 (m, 2H), 4.12 (brs., 1H), 3.84 (dd, J=3.2, 9.9 Hz, 1H), 3.76 (t, J=9.2 Hz, 1H), 3.69-3.61 (m, 2H), 3.29 (ddd, J=4.3, 9.2, 14.0 Hz, 1H); $^{13}$C NMR (125 MHz, CHLOROFORM-d) $\delta_C$=163.1, 140.9, 138.4, 138.1, 137.3, 128.5, 128.4, 128.0, 127.7, 127.6, 127.6, 127.5, 124.2, 73.6, 73.5, 73.3, 71.5, 69.6, 68.9, 59.3, 47.0; ESI-MS: m/z 480.11 (M+Na)$^+$; HRMS: m/z calcd for $C_{29}H_{31}NO_4Na$ 480.2145, found 480.2141.

Example 29: General Procedure for Dihydroxylation; Synthesis of 30/33/34

To a vigorously stirred solution of compound (22b/24b/27b)(46.5 mg, 0.113 mmol) in CH$_3$CN (1.2 ml) at 0-5° C. was added a solution of RuCl$_3$.3H$_2$O (15 ul, 0.1 M aq 0.105 eq) and NaIO$_4$ (48 mg, 0.226 mmol, 2 eq) in distilled water (0.2 ml). The mixture was stirred for 35 min by complete consumption of starting material (TLC). The suspension was when filtered through a thin pad of silica gel, which was washed with ethyl actate (20 ml). Concentration of the filtrate and flash chromatography gave the diol.

Example 30: (3S,4R,5R,6R)-1-benzyl-5-(benzyloxy)-6-((benzyloxy)methyl)-3,4-dihydroxypiperidin-2-one. (30)

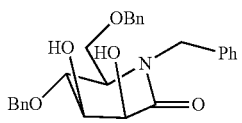 [SMILES: O=C1C(O)C(O)C(OCc2ccccc2)C(COCc2ccccc2)N1Cc1ccccc1]

Colorless oil, $C_{27}H_{29}NO_5$, $R_f$ 0.6 (EtOAc-petroleum ether, 7:3); $[\alpha]^{25}_D$ +12.96 (c 1.6 CHCl$_3$); IR (CHCl$_3$): $v_{max}$ 3443, 3066, 3018, 2926, 2401, 2361, 1722, 1641, 1453, 1215, 1075, 1029, 757, 699, 669 cm$^{-1}$; 35 min, yield 43%. Flash chromatography Elution with 20-25% EtOAc-petroleum ether; $^1$H NMR (400 MHz, CHLOROFORM-d) $\delta_H$=7.39-7.25 (m, 10H), 7.21-7.04 (m, 5H), 5.27 (d, J=15.4 Hz, 1H), 4.51-4.39 (m, 5H), 4.38-4.29 (m, 2H), 3.96 (t, J=2.9 Hz, 1H), 3.78-3.70 (m, 2H), 3.66 (s, 1H), 3.08 (br. s., 1H); $^{13}$C NMR (100 MHz, CHLOROFORM-d) 6=$^{13}$C NMR (101 MHz, CHLOROFORM-d) $\delta_C$=171.2, 137.4, 137.2, 136.8, 128.6, 128.5, 128.5, 128.0, 127.9, 127.8, 127.3, 75.2, 73.2, 71.6, 69.5, 68.9, 68.1, 59.0, 47.6; ESI-MS: m/z 448.2 (M+H)$^+$; HRMS: m/z calcd for $C_{27}H_{29}NO_5Na$ 470.1938 found 470.1937.

Example 31: (3S,4R,5R,6R)-5-(benzyloxy)-6-((benzyloxy)methyl)-1-butyl-3,4-dihydroxy-piperidin-2-one. (33)

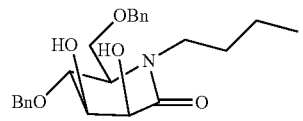 [SMILES: CCCCN1C(=O)C(O)C(O)C(OCc2ccccc2)C1COCc1ccccc1]

Pale yellow oil, $C_{24}H_{31}NO_5$, $R_f$ 0.3 (EtOAc-petroleum ether, 1:1); $[\alpha]^{25}_D$ -0.89 (c 0.75, CHCl$_3$); IR (CHCl$_3$): $v_{max}$ 3411, 3066, 3016, 2959, 2928, 2858, 1724, 1638, 1494, 1367, 1300, 1216, 1028, 757, 698, 667 cm$^{-1}$; 45 min, yield 46%. Flash chromatography Elution with 15-25% EtOAc-petroleum ether; $^1$H NMR (400 MHz, CHLOROFORM-d) $\delta_H$ 7.40-7.21 (m, 10H), 4.65-4.59 (m, 2H), 4.51-4.45 (m, 2H), 4.30 (dd, J=10.3, 3.2 Hz, 2H), 4.00 (brs., 1H), 3.93-3.75 (m, 3H), 3.74-3.68 (m, 1H), 3.68-3.60 (m, 1H), 3.12-3.00 (m, 1H), 2.86 (brs, 1H), 1.58-1.43 (m, 2H), 1.33-1.27 (m, 2H), 0.88 (t, J=7.1 Hz, 3H); $^{13}$C NMR (101 MHz, CHLOROFORM-d) $\delta_C$ 170.5, 137.5, 137.4, 128.5, 128.0, 127.9, 127.8, 75.0, 73.3, 71.8, 69.5, 68.6, 67.8, 60.1, 44.8, 29.6, 20.0, 13.8; ESI-MS: m/z 436.11 (M+Na)$^+$; HRMS: m/z calcd for $C_{24}H_{31}NO_5Na$ 436.2094, found 436.2088.

Example 32: (3S,4R,5R,6R)-5-(benzyloxy)-1-(2-(benzyloxy)ethyl)-6-((benzyloxy) methyl)-3,4-dihydroxypiperidin-2-one. (34)

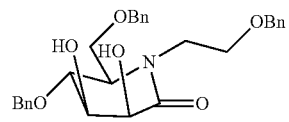

Pale yellow oil, $C_{29}H_{33}NO_6$, $R_f$ 0.37 (EtOAc-petroleum ether, 7:3); $[\alpha]^{25}_D$ +17.25 (c 1.07, CHCl$_3$); IR (CHCl$_3$): $v_{max}$ 3410, 3066, 3015, 2922, 2853, 1723, 1640, 1495, 1454, 1365, 1216, 1028, 757, 698, 667 cm$^{-1}$; 55 min, yield 57%. Flash chromatography Elution with 30-40% EtOAc-petroleum ether; $^1$H NMR (400 MHz) $\delta_H$=7.35-7.24 (m, 15H), 4.61-4.51 (m, 2H), 4.51-4.41 (m, 4H), 4.31 (s, 2H), 4.02 (td, J=14.2, 4.5 Hz, 1H), 3.93 (brs, 1H), 3.87 (d, J=6.6 Hz, 3H), 3.77-3.70 (m, 1H), 3.68-3.56 (m, 2H), 3.51-3.42 (m, 1H), 2.85 (brs, 1H), 1.61 (brs, 1H); $^{13}$C NMR (100 MHz, CDCl$_3$) $\delta_C$=170.9, 138.1, 137.5, 137.4, 128.5, 128.4, 128.0, 127.9, 127.8, 127.8, 127.6, 127.6, 75.3, 73.2, 71.6, 69.1, 68.8, 68.2, 68.0, 60.3, 44.7; ESI-MS: m/z 514.2 (M+Na)$^+$; HRMS: m/z calcd for $C_{29}H_{33}NO_6Na$ 514.2200, found 514.2198.

Example 33: (5S,6R)-1-benzyl-5-(benzyloxy)-6-((benzyloxy)methyl)piperidin-2-one. (29)

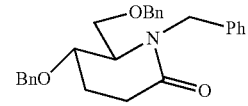 [SMILES: O=C1CCC(OCc2ccccc2)C(COCc2ccccc2)N1Cc1ccccc1]

A solution of 24b (37 mg, 0.089 mmol) in methanol (3 ml) was cooled to 0° C. and treated with NiCl$_2$.6H$_2$O (16 mg, 0.066 mmol). The resulting mixture was stirred at the same temperature for 15 min before the addition of NaBH$_4$ (2.6 mg, 0.066 mmol). After 30 min, further portion of NaBH$_4$ (2.6 mg, 0.066 mmol) was added, and the reaction was allowed to stir for additional 10 min at 20° C. The reaction was quenched with a saturated solution of NH$_4$Cl (5 ml) and extracted with CH$_2$Cl$_2$ (3×10 ml). The combined extracts were dried (MgSO$_4$) and concentrated under vacuum. Flash column chromatography (silica gel, 20-30% EtOAc in hexanes) afforded as a colourless oil C$_{27}$H$_{29}$NO$_3$(24 mg, 66% yield). Rf=0.61 (silica gel, ethyl acetate/hexanes, 7:3). $[\alpha]^{25}_D$ +49.11 (c 1.08 CHCl$_3$); IR (CHCl$_3$): $\nu_{max}$ 3443, 3087, 3066, 3031, 2965, 2854, 1642, 1455, 1248, 1096, 756, 698, 666 cm$^{-1}$; 26 h, 2.5 h, yield 66%. Flash chromatography Elution with 20-25% EtOAc-petroleum ether.

$^1$H NMR (400 MHz, CHLOROFORM-d) $\delta_H$=7.40-7.10 (m, 15H), 5.36 (d, J=15.2 Hz, 1H), 4.48-4.34 (m, 3H), 4.33-4.24 (m, 1H), 4.00 (d, J=15.2 Hz, 1H), 3.91-3.82 (m, 1H), 3.66 (td, J=3.1, 6.7 Hz, 1H), 3.55 (dd, J=4.0, 9.9 Hz, 1H), 3.42 (dd, J=7.1, 10.0 Hz, 1H), 2.78-2.63 (m, 1H), 2.49-2.35 (m, 1H), 2.09-1.93 (m, 2H). $^{13}$C NMR (101 MHz, CHLOROFORM-d) $\delta_C$=170.3, 138.1, 137.6, 137.2, 128.5, 128.5, 128.3, 127.9, 127.8, 127.6, 127.3, 127.2, 73.3, 72.0, 70.1, 69.4, 58.6, 48.0, 27.4, 22.4. ESI-MS: m/z 416.3 (M+H)$^+$; HRMS: m/z calcd for C$_{27}$H$_{30}$NO$_3$ 416.2220 found 416.2217.

Example 34: General Procedure for Reduction of Lactams Carbonyl Using BH$_3$.SMe$_2$; Synthesis of 32/35/36

To an ice-cold solution of lactam(30/33/34)(0.16 mmol) in dry THF (5 mL) was added BH$_3$.SMe$_2$ (1.7 mL, 3.28 mmol 2.0 M in THF) dropwise under argon, and the reaction mixture was kept at room temperature for 8 h. The excess of reducing agent was quenched by slow addition of EtOH (5 mL). After evaporation of the solvent, the residue was dissolved in EtOH (10 mL) and heated at reflux for 2 h. The cooled mixture was then evaporated and subjected to flash chromatography.

Example 35: (3R,4R,5R,6R)-1-benzyl-5-(benzyloxy)-6-((benzyloxy)methyl) piperidine-3,4-diol. (32)

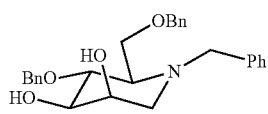

Pale yellow oil, C$_{27}$H$_{31}$NO$_4$, R$_f$ 0.51 (MeOH-DCM, 1:9); $[\alpha]^{25}_D$ −10.61 (c 1.1 CHCl$_3$); IR (CHCl$_3$): $\nu_{max}$ 3408, 3064, 3011, 2926, 2856, 2361, 2340, 1657, 1453, 1216, 1104, 1074, 756, 699, 667 cm$^{-1}$; yield 41%. Flash chromatography elution with 0-5% MeOH-DCM.

$^1$H NMR (400 MHz, CHLOROFORM-d) $\delta_H$=7.39-7.27 (m, 15H), 4.91 (d, J=11.0 Hz, 1H), 4.56 (d, J=11.0 Hz, 1H), 4.46 (s, 2H), 4.18 (d, J=13.2 Hz, 1H), 3.89-3.72 (m, 3H), 3.66 (t, J=8.4 Hz, 2H), 3.57 (d, J=8.3 Hz, 1H), 3.29 (d, J=13.2 Hz, 1H), 2.93 (dd, J=3.2, 12.2 Hz, 1H), 2.58 (br. s., 1H), 2.39 (d, J=8.3 Hz, 1H), 2.23 (d, J=12.5 Hz, 1H); $^{13}$C NMR (100 MHz, CHLOROFORM-d) $\delta_C$=138.5, 138.3, 137.8, 129.1, 128.5, 128.1, 127.9, 127.7, 127.3, 78.3, 75.9, 74.7, 73.3, 68.1, 66.7, 64.8, 56.7, 54.7; ESI-MS: m/z 434.2 (M+H); HRMS: m/z calcd for C$_{27}$H$_{32}$NO$_4$ 434.2326, found 434.2327.

Example 36: (3R,4R,5R,6R)-5-(benzyloxy)-6-((benzyloxy)methyl)-1-butyl piperidine-3,4-diol. (35)

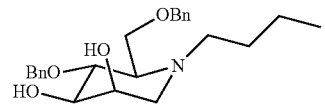 [SMILES: CCCCN1CC(O)C(O)C(OCc2ccccc2)C1COCc1ccccc1]

Pale yellow oil, C$_{24}$H$_{33}$NO$_4$, R$_f$ 0.46 (MeOH-DCM, 1:9); $[\alpha]^{25}_D$ −14.73 (c 0.7 CHCl$_3$); IR (CHCl$_3$): $\nu_{max}$ 3384, 3066, 3014, 2961, 2931, 2873, 1641, 1496, 1454, 1216, 1076, 1028, 757 cm$^{-1}$; yield 32%. Flash chromatography Elution with 0-4% MeOH-DCM; $^1$H NMR (500 MHz, CHLOROFORM-d) $\delta_H$=7.40-7.21 (m, 10H), 4.93 (d, J=11.0 Hz, 1H), 4.58-4.41 (m, 3H), 4.02 (br. s., 1H), 3.91-3.80 (m, 1H), 3.80-3.58 (m, 3H), 3.47-3.28 (m, 2H), 3.28-3.18 (m, 1H), 2.94 (br. s., 1H), 2.80 (br. s., 1H), 2.70 (d, J=10.4 Hz, 1H), 2.66-2.59 (m, 1H), 1.57-1.42 (m, 2H), 1.31-1.27 (m, 1H), 1.23-1.16 (m, 1H), 0.87 (t, J=7.3 Hz, 3H); $^{13}$C NMR (100 MHz, CHLOROFORM-d) $\delta_C$=138.1, 137.3, 128.5, 128.5, 128.2, 128.1, 128.0, 127.8, 75.0, 73.3, 67.3, 65.6, 63.7, 54.7, 52.8, 25.8, 20.2, 13.8; ESI-MS: m/z 400.1 (M+H); HRMS: m/z calcd for C$_{24}$H$_{34}$NO$_4$ 400.2482, found 400.2482.

Example 37: (3R,4R,5R,6R)-5-(benzyloxy)-1-(2-(benzyloxy)ethyl)-6-((benzyloxy) methyl) piperidine-3,4-diol. (36)

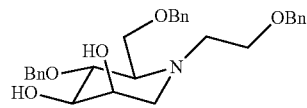 [SMILES: OC1CN(CCOCc2ccccc2)C(COCc2ccccc2)C(OCc2ccccc2)C1O]

Pale yellow oil, C$_{29}$H$_{35}$NO$_5$, R$_f$ 0.54 (MeOH-DCM, 1:9); $[\alpha]^{25}_D$ −4.85 (c 0.76 CHCl$_3$); IR (CHCl$_3$): $\nu_{max}$ 3396, 3018, 2927, 2857, 1641, 1497, 1216, 1072, 758 cm$^{-1}$; yield 30%. Flash chromatography elution with 0-4% MeOH-DCM; $^1$H NMR (500 MHz, CHLOROFORM-d) $\delta_H$=7.38-7.26 (m, 15H), 4.88 (d, J=11.3 Hz, 1H), 4.53-4.38 (m, 6H), 3.84 (br. s., 1H), 3.77-3.69 (m, 2H), 3.61-3.50 (m, 4H), 3.15-3.04 (m, 2H), 2.91 (td, J=5.4, 14.3 Hz, 1H), 2.62 (d, J=12.2 Hz, 1H), 2.45 (d, J=8.5 Hz, 2H).

$^{13}$C NMR (125 MHz, CHLOROFORM-d) $\delta_C$=138.4, 138.1, 137.7, 128.6, 128.5, 128.5, 128.1, 128.1, 127.9, 127.9, 127.7, 127.7, 78.1, 76.0, 74.8, 73.3, 73.2, 68.3, 67.2, 66.4, 64.0, 56.1, 51.5; ESI-MS: m/z 500.2 (M+Na)$^+$; HRMS: m/z calcd for C$_{29}$H$_{36}$NO$_5$ 478.2588, found 478.2587.

Advantages of the Invention

1. Novel compounds that can be converted into the corresponding bioactive piperidine alkaloids and their analogues.
2. One step protocol for N-alkylation and regioselective debenzylation for preparation of N-alkylation of glycolactam compounds.

We claim:
1. A compound of Formula I,

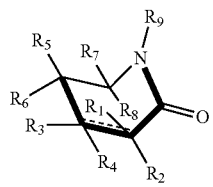

wherein, each of $R_1$, $R_2$, $R_3$, $R_4$, $R_5$, $R_6$, $R_7$ and $R_8$ are independently selected from the group consisting of OBn, OH, $CH_2OBn$, $CH_2OH$, $CH_3$; and
$R_9$ is selected from the group consisting of alkyl, substituted alkyl, alkenyl, hydroxyl alkyl, and benzyl.

2. The compound as claimed in claim 1, wherein said compound is

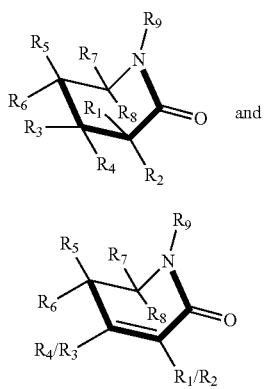

wherein, each of $R_1$, $R_2$, $R_3$, $R_4$, $R_5$, $R_6$, $R_7$ and $R_8$ are independently selected from the group consisting of OBn, OH, $CH_2OBn$, $CH_2OH$, $CH_3$; and
$R_9$ is selected from the group consisting of alkyl, substituted alkyl, alkenyl, hydroxyl alkyl, and benzyl.

3. The compound as claimed in claim 1, wherein said compound is:
(4R,5R,6R)-4,5-bis(benzyloxy)-6-((benzyloxy)methyl)-1-methylpiperidin-2-one (3a);
(4R,5S,6R)-4,5-bis(benzyloxy)-6-((benzyloxy)methyl)-1-methylpiperidin-2-one (4a);
(4R,5R,6R)-4,5-bis(benzyloxy)-6-((benzyloxy)methyl)-1-ethylpiperidin-2-one (5a);
(4R,5S,6R)-4,5-bis(benzyloxy)-6-((benzyloxy)methyl)-1-ethylpiperidin-2-one (6a);
(4R,5R,6R)-4,5-bis(benzyloxy)-6-((benzyloxy)methyl)-1-propyl piperidine-2-one (7a);
(4R,5S,6R)-4,5-bis(benzyloxy)-6-((benzyloxy)methyl)-1-propylpiperidin-2-one (8a);
(4R,5R,6R)-4,5-bis(benzyloxy)-6-((benzyloxy)methyl)-1-butylpiperidin-2-one (9a);
(4R,5S,6R)-4,5-bis(benzyloxy)-6-((benzyloxy)methyl)-1-butylpiperidin-2-one (10a);
(4R,5R,6R)-1-benzyl-4,5-bis(benzyloxy)-6-((benzyloxy)methyl)piperidin-2-one (1a);
(4R,5R,6R)-1-allyl-4,5-bis(benzyloxy)-6-((benzyloxy)methyl)piperidin-2-one (12a);
(4R,5S,6R)-1-allyl-4,5-bis(benzyloxy)-6-((benzyloxy)methyl)piperidin-2-one (13a);
(4R,5R,6R)-4,5-bis(benzyloxy)-1-(2-(benzyloxy)ethyl)-6-((benzyloxy)methyl)piperidin-2-one (14a);
(4R,5S,6R)-4,5-bis(benzyloxy)-1-(2-(benzyloxy)ethyl)-6-((benzyloxy)methyl)piperidin-2-one (15a);
(5S,6R)-5-(benzyloxy)-6-((benzyloxy)methyl)-1-methyl-5,6-dihydropyridin-2(1H)-one (16b);
(5R,6R)-5-(benzyloxy)-6-((benzyloxy)methyl)-1-methyl-5,6-dihydropyridin-2(1H)-one (17b);
(5S,6R)-5-(benzyloxy)-6-((benzyloxy)methyl)-1-ethyl-5,6-dihydropyridin-2(1H)-one (18b);
(5R,6R)-5-(benzyloxy)-6-((benzyloxy)methyl)-1-ethyl-5,6-dihydropyridin-2(1H)-one (19b);
(5S,6R)-5-(benzyloxy)-6-((benzyloxy)methyl)-1-propyl-5,6-dihydropyridin-2(1H)-one (20b);
(5R,6R)-5-(benzyloxy)-6-((benzyloxy)methyl)-1-propyl-5,6-dihydropyridin-2(1H)-one (21b);
(5S,6R)-5-(benzyloxy)-6-((benzyloxy)methyl)-1-butyl-5,6-dihydropyridin-2(1H)-one (22b);
(5R,6R)-5-(benzyloxy)-6-((benzyloxy)methyl)-1-butyl-5,6-dihydropyridin-2(1H)-one (23b);
(5S,6R)-1-benzyl-5-(benzyloxy)-6-((benzyloxy)methyl)-5,6-dihydropyridin-2(1H)-one (24b);
(5S,6R)-1-allyl-5-(benzyloxy)-6-((benzyloxy)methyl)-5,6-dihydropyridin-2(1H)-one (25b);
(5R,6R)-1-allyl-5-(benzyloxy)-6-((benzyloxy)methyl)-5,6-dihydropyridin-2(1H)-one (26b);
(5S,6R)-5-(benzyloxy)-1-(2-(benzyloxy)ethyl)-6-((benzyloxy)methyl)-5,6-dihydropyridin-2(1H)-one (27b); or
(5R,6R)-5-(benzyloxy)-1-(2-(benzyloxy)ethyl)-6-((benzyloxy)methyl)-5,6-dihydropyridin-2(1H)-one (28b).

4. A process for preparation of an N-alkylated glycolactam compound of claim 1, wherein said process comprises:
a) adding a metal hydride to a solution of glycolactamine solvent at a temperature ranging from 0° C. to 5° C. to form a reaction mixture followed by stirring said reaction mixture at a temperature ranging from 0° C. to 5° C. for a time period ranging from 10 to 15 minutes; and,
b) adding an alkyl halide to said reaction mixture at a temperature ranging from 0° C. to 5° C. followed by stirring said reaction mixture at temperature ranging from 0° C. to 5° C. for a time period ranging from 2 to 48 hours to form the N-alkylated glycolactam of formula I.

5. The process as claimed in claim 4, wherein said metal hydride is selected from the group consisting of sodium hydride, potassium hydride and calcium hydride.

6. The process as claimed in claim 4, wherein said solvent of step a) is selected from the group consisting of dimethyl formamide, dimethyl sulfoxide, and tetrahydrofuran.

7. The process as claimed in claim 4, wherein said alkyl halide is selected from the group consisting of methyl iodide, ethyl bromide, allyl bromide, n-butyl iodide, benzyl bromide, n-propyl bromide and benzyloxy 2-ethyliodide.

8. A process for the synthesis of a piperidine alkaloid or an analogue thereof from a compound of claim 1, comprising:
a) adding a solution of ruthenium (III) chloride hydrate and sodium periodate in distilled water to a solution of a glycolactam compound of formula IB in acetonitrile at a temperature ranging from 0° C. to 5° C. to form a reaction mixture;
b) stirring the reaction mixture for a time period ranging from 30 to 40 minutes at a temperature ranging from 0° C. to 5° C. to form a dihydroxylated compound of a glycolactam compound of formula IB;

c) adding Pd/C to said solution of said dihydroxylated glycolactam compound of formula IB in methanol/ethanol/ethyl acetate followed by stirring for a time period ranging from 14 to 16 hours at a temperature ranging from 30 to 35° C. under a hydrogen atmosphere to form a Mannolactam;

d) alternatively, adding borane dimethyl sulphide to a solution of a dihydroxylated compound of a glycolactam compound of formula IB in a solvent at a temperature ranging from 0° C. to 5° C. for 1 to 2 hours followed by stirring at a temperature ranging from 30 to 35° C. for 4 to 6 hours followed by stirring at a reflux temperature for a time period ranging from 2 to 4 hours, to obtain a piperidine derivative of formula IB;

e) adding Pd/C to a solution of said piperidine derivative of formula IB in methanol/ethanol/ethyl acetate followed by stirring for a time period ranging from 14 to 16 hours at a temperature ranging from 30 to 35° C. under hydrogen atmosphere to form a benzyl protected deoxymannojirimycin;

f) hydrogenating said benzyl protected deoxymannojirimycin by a hydrogenating agent in a solvent to form a deoxynojirimycin;

g) alternatively, adding nickel(II) chloride hexahydrate to a cooled solution of the glycolactam compound of formula IB in an alcohol followed by stirring for 10 to 15 minutes at a temperature ranging from 0° C. to 5° C. to obtain a solution;

h) adding sodium borohydride to said solution of step (g) at a temperature ranging from 0° C. to 5° C. for a time period ranging from 10 to 15 minutes; followed by stirring for 2 to 2.5 hours at a temperature ranging from 25 to 30° C. to obtain a saturated glycolactum product;

i) adding Lawesson's reagent to a solution of the saturated glycolactum product of step (h) in THF or dioxane followed by stirring said solution for a time period ranging from 4 to 12 hours to form a thiolactum;

j) stirring a solution of said thiolactam of step (i) and 1-bromoethyl acetate in diethylether or dichloromethane for a time period ranging from 24 to 36 hours, removing said solvent to form a thionium salt, adding triphenylphosphine to a solution of said thionium salt in acetonitrile followed by stirring for a time period ranging from 10 to 15 minutes by further adding triethyl amine to the reaction mixture followed by heating at a temperature ranging from 70 to 75° C. for a time period ranging from 26 to 27 hours and filtering the product to form an enamide;

k) stirring the enamide of step (j) in a mixture of sodium carbonate and 10% palladium on carbon in ethanol or methanol under an atmosphere of hydrogen for a time period ranging from 16 to 48 hours to form a piperidine ester;

l) alternatively, adding sodium cyanoborohydride to a solution of the enaminoester and bromocresol green in methanol, adding 5% methanolic HCl solution drop wise until a yellow color persists in solution, stirring said solution for a time period ranging from 2 to 3 hours, periodically adding HCl to maintain a yellow color, diluting the mixture with $CH_2Cl_2$, washing with 10% aqueous $NaHCO_3$ to form a piperidine ester;

m) adding lithium aluminum hydride to a solution of the piperidine ester of step (k) or piperidine ester of step (l) in diethylether or tertrahydrofuran followed by stirring for a time period ranging from 2 to 4 hours, quenching the reaction by adding water and 15% aqueous NaOH, stirring the mixture for a time ranging from 1 to 2 hours to form a piperidin alcohol;

n) adding a solution of dimethyl sulfoxide in dicholoromethane to a solution of oxalyl chloride in dicholoromethane at a temperature ranging from –70° C. to –80° C. for a time period ranging from 10 to 11 hours, adding a solution of piperidine alcohol of step (m) in dichoromethane to said reaction mixture, followed by stirring for 45 to 50 minutes at a temperature ranging from –65° C. to –70° C., adding trimethylamine to said solution followed by stirring for a time period ranging from 20 to 30 minutes at a temperature ranging from –65° C. to –70° C. and then warming said solution to room temperature for a time period ranging from 1 to 2 hours to form a piperidine aldehyde;

o) refluxing a mixture of 2-(7-bromoheptyl)-2-ethyl-1,3-dioxolane and triphenylphosphine in toluene for a time period ranging from 40 to 50 hours, cooling the solution to room temperature, removing the solvent, adding tetrahydrofuran to said mixture and adding a solution of butyl lithium in hexane to the phoshonium salt at a temperature ranging from –78° C. to –80° C. followed by stirring for 10 to 20 minutes at –78° C. and then continuing the stirring for a time period ranging from 1 to 3 hours at a temperature ranging from 25° C. to 30° C., cooling the resulting yield solution to –78° C. and adding the piperidine aldehyde of step q (n) in tetrahydrofuran, followed by warming the mixture to –45° C. over 2 to 4 hours, continuing the stirring for an additional 1 to 2 hours at –45° C., warming to 0° C. for 3 to 5 hours, and stirring an additional 2 to 4 hours at a temperature ranging from 25° C. to 30° C. to form a condensed product;

p) adding hydrochloric acid to said solution of the above condensed product of step (o) in tetrahydrofuran, followed by stirring for 2 to 4 hours, adding saturated aqueous sodium bicarbonate and extracting the mixture dichloromethane, drying and concentrating the organic layers to obtain a residue, dissolving the residue in ethanol or methanol and adding conc. HCl, adding 10% Pd on carbon followed by stirring under $H_2$ at 3 atm pressure for 20 to 30 hours to obtain (+)-Prosophylline or (+)-Prosopinine compounds.

9. The process as claimed in claim 8, wherein said bioactive piperidine alkaloid or analogues thereof is selected from the group consisting of Mannolactam, Deoxymannojirimycin, N-butyl deoxymannojirimycinMiglustat, N-(2-hydroxyethyl)deoxymannojirimycin, Miglitol, (+)-Prosophylline, (+)-Prosopinine, 3-epi-N-butyl deoxymannojirimycin, and 3-epi-N-(2-hydroxyethyl)deoxymannojirimycin.

* * * * *